United States Patent [19]

Groutas

[11] Patent Number: 5,550,139
[45] Date of Patent: Aug. 27, 1996

[54] SERINE PROTEASE INHIBITORS

[75] Inventor: William C. Groutas, Wichita, Kans.

[73] Assignee: The Wichita State University, Wichita, Kans.

[21] Appl. No.: 177,352

[22] Filed: Jan. 3, 1994

[51] Int. Cl.$^6$ .................. C07D 285/10; C07D 275/03; A61K 31/41
[52] U.S. Cl. .................. 514/362; 514/372; 548/135; 548/213
[58] Field of Search .................. 548/213, 135; 514/372, 362

[56] References Cited

U.S. PATENT DOCUMENTS

| | | | |
|---|---|---|---|
| 4,785,010 | 11/1988 | Zoller et al. | 514/362 |
| 5,306,818 | 4/1994 | Subramanyam et al. | 574/135 |

OTHER PUBLICATIONS

Aouf et al., "Synthese Et Cyclisation De Carboxylsulfamides Derives D'Aminoacides", Tetrahedron Letters, 32:6545–6546, 1991.
Dallegri et al., "Effect of Nonsteroidal Antinflammatory Drugs on the Neutrophil Promoted Inactivation of Alpha–1–Proteinase Inhibitor", J. Rheumatology, 19:419–423, 1992.
Doherty et al., "Cephalosporin antibiotics can be modified to inhibit human leukocyte elastase", Nature, 322:192–194, 1986.
Groutas et al., "Inhibitors of Human Neutrophil Cathepsin G: Structural and Biochemical Studies", Archives of Biochemistry and Biophysics, 294:144–146, 1992.
Groutas et al., "$^{13}$C NMR Evidence for an Enzyme–Induced Lossen Rearrangement in the Mechanism–Based Inactivation of . . . 3–Benzyl–N–((methylsulfonyl)oxy)succinimide", J. Am. Chem. Soc., 111:1932–1933, 1989.
Groutas et al., "Hydantoin Derivatives. A New Class of Inhibitors of Human Leukocyte Elastase," J. Enzyme Inhibition, 3:237–243, 1990.
Groutas et al., "Potential Mechanism–Based Inhibitors of Proteolytic Enzymes," Bioorganic & Medicinal Chemistry Letters 2:175–180, 1992.
Groutas et al., "Novel Potential Mechanism–Based Inhibitors of Human Leukocyte Elastase and Catheps in G:Derivatives of Isothiazolidin–3–One", Biochem. and Biophys. Res. Comm., 197:730–739, 1993.
Groutas et al., "Inhibition of Human Leukocyte Elastase by Derivatives of N–Hydroxysuccinimide A Structure–Activity–Relationship Study", J. Med. Chem., 32:1607–1611, 1989.

Groutas et al., "Dual–Action Inhibitors of Proteolytic Enzymes: Potential Therapeutic Agents for Cystic Fibrosis and Related Ailments", Bioorganic & Medicinal Chemistry, 1:273–277, 1993.
Groutas et al., "Mechanism–Based Inhibitors of Serine Proteinases Based on the Gabriel–Colman Rearrangement" Biochemical and Biophysical Research Communications, 194:1491–1499, 1993.
Groutas et al. "Efficient Inhibition of Human Leukocyte Elastase and Catheps in G by Saccharin Derivatives", J. Med. Chem., 36:3173–3176, 1993.
Hagman, Annual Reports in Medicinal Chemistry, 28:187–195, 1993.
Kao et al., "Proteinase 3 A Distinct Human Polymorphonuclear Leukocyte Proteinase that Produces Emphusema in Hamsters", J. Clin. Invest., 82:1963–1972, 1988.
Leder et al., "Consequences of Widespread Deregulation of the c–myc Gene in Transgenic Mice: Multiple Neoplasms and Normal Development", Cell, 45:485–495, 1986.
Lee et al., "3–Oxo– and 3–Imino–4–substituted–1,2,5–thiadiazolidine 1,1–Dioxides: Synthesis, Spectral Properties, and Selected Chemistry", J. Org. Chem., 54:3077–3083, 1989.
Lehrer et al., "Neutrophils and Host Defense", Annals of Internal Medicine, 109:127–142, 1988.
Malech et al., "Current Concepts: Immunology. Neutrophils in Human Diseases," The New England Journal of Medicine, 317:687–694, 1987.
Nakagawa et al., "Anti–Inflammatory Effect of a Selective Inhibitor of Elastase, Catheps in G and Chymotrypsin G and . . . in Rats", J. Pharmacobio–Dyn., 9:432–435, 1986.
Shin et al., "Dehydrooligopeptides. XIV. Convenient Coupling of N–Carboxy–α–dehydroamino Acid Anhydride with Both Amine and Carboxyl Componants", Bull. Chem. Soc. Jpn., 66:1844–1846, 1993.
Trainor, "Synthetic inhibitors of human neutrophil elastase", TIPS, 8:303–307, 1987.
Ueno et al., "Deacylative Condensation I. A New Facile Method for the Direct α–Methylenation of Ester or Lactone Starting from . . . Compounds," Tetrahedron Letters 39:3753–3756, 1978.
Weiss, "Tissue Destruction by Neutrophils", New England Journal Medicine, 320:365–376, 1989.
Gunther, Chem Ber. 103 663 (1970).

*Primary Examiner*—Robert Gerstl
*Attorney, Agent, or Firm*—Fish & Richardson P.C.

[57] ABSTRACT

Isothiazolidin-3-one-1,1 dioxide, 3-oxo-1,2,5-thiadiazolidine-1,1,-dioxide and derivatives thereof, reduce or inhibit the activity of serine proteases. Such compounds are useful as anti-inflammatory and anti-metastatic agents.

19 Claims, 8 Drawing Sheets

$^a$H-CO-H/NaOEt; $^b$CH$_3$-CO-SH; $^c$H$_2$O$_2$/HCOOH;
$^d$PCl$_3$; $^e$NH$_4$OH; $^f$NaH/THF; $^g$F-CH$_2$-CHCl-SPh/TEA;
$^h$m-chloroperbenzoic acid (2 eq)/CH$_2$Cl$_2$;
$^i$silica gel/CH$_2$Cl$_2$; $^j$PhSCH$_2$Cl/TEA then
m-chloroperbenzoic acid (2.2 eq)/CH$_2$Cl$_2$

[a] DCC (dicyclohexy carbodiimide) /pyridine/methylene chloride
t-Boc-L-alanine

[b] m-chloroperbenzoic acid
(TFA = trifluoroacetic acid)

SERINE PROTEASE INHIBITORS

STATEMENT AS TO FEDERALLY SPONSORED RESEARCH

This work was supported by a grant from the National Institutes of Health (HL 38048). The U.S. government has certain rights to this invention.

BACKGROUND OF THE INVENTION

Inflammation is associated with tissue trauma, peritonitis, colitis, enteritis, vasculitis, pulmonary emphysema, cystic fibrosis, chronic pulmonary infection, bronchitis, psoriasis, arthritis, rheumatoid arthritis, allergic contact dermatitis, atopic dermatitis, glomerulonephritis, ARDS, pancreatitis and sepsis, among other inflammatory states (reviewed in Weiss, S. J. *N. Engl. J. Med.* 320, 365, (1989); Lehrer, R. I. et al. *Ann. Intern. Med.* 109, 127 (1988); Malech, H. L. et al. *Ann. Intern. Med.* 317, 687, (1987)). The chemotaxis and accumulation of neutrophils (i.e., neutrophil diapedesis), as well as the release of antibiotic proteins (e.g., defensins), proteolytic enzymes (e.g., serprocidins), and granule-based toxins are associated with inflammation (reviewed in Syntex Research Canada *Annual Reports in Med. Chem.* 28, 187–195 (1993)). The unmodulated activity of proteolytic enzymes, and neutrophil diapedesis are important causes of inflammation.

The serprocidins include serine proteinases such as human leukocyte elastase (i.e. HLE), cathepsin G (i.e. Cath G) and proteinase 3 (i.e. PR-3). Inflammation can be reduced by the presence of biological inhibitors such as alpha-1-proteinase inhibitor, secretory leukocyte protease inhibitor, and elafin. Synthetic agents capable of reducing serine protease activity are of therapeutic value as anti-inflammation drugs (Snider, *Drug. Dev. Res.* 10:235–253, 1987; Wewers et al., *New Engl. J. Med.* 316:1055–1062, 1987; McElvaney et al., *Lancet* 337:392–394, 1991; McElvaney et al., *Am. Rev. Resp. Dis.* 145(4)part 2, suppl.; Weinbaum et al., *In Focus on Pulmonary Pharmacology and Toxicology*, Hollinger, ed., CRC Press, Boca Raton, Fla., 1991; Krantz in *Ann. Rep. Med. Chem.*, Bristol, ed., Vol. 28, pp. 187–195, Academic Press, Inc., San Diego, Calif., 1993). Examples of compounds that have been used to inhibit serine proteinases include derivatives of isocoumarin and cephalosporin (Hernandez et al., *J. Med. Chem.* 35:1121–1129, 1993; Knight et al., *Biochemistry* 31:4980–4986, 1992) haloenol lactones (Rai et al., *J. Med. Chem.* 35:4150–4159, 1992), substituted succinimides and related compounds (Groutas et al., *J. Med. Chem.* 32:1607–1611, 1989; Groutas et al., *J. Am. Chem. Soc.* 111: 1931–1932, 1989; Groutas et al., *J. Enzyme Inhibition* 3:237–243, 1990; Groutas et al., *BioMed. Chem. Lett.* 2:1565–1570, 1992), ynenol lactones (Copp et al., *Biochemistry* 7:169–178, 1987), and derivatives of saccharin (Groutas, W. C. et al. *Bioorg. & Med. Chem.* 1(4) 273–277 (1993); Groutas et al. *J. Med. Chem.* 36, 3178–3181 (1993).

SUMMARY OF THE INVENTION

In general, the invention features a compound represented by the following formula:

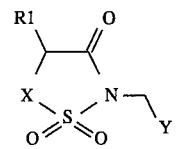

wherein:

a) X is CH2 or NR2 where R2 is any one of H, alkyl, halogen substituted alkyl, alkenyl, halogen substituted alkenyl, alkynyl, halogen substituted alkynyl, halogen substituted alkanoate, alkoxy, Ph-alkyl-, Ph-alkenyl-, Ph-alkynyl-, Ph—S-alkyl-, Ph—S-alkenyl-, Ph—S-alkynyl-, Ph—SO—, Ph—SO$_2$—, P—SO$_2$-alkyl-, Ph—SO$_2$-alkenyl-, Ph—SO$_2$-alkynyl-, benzyl, alkyl substituted benzyl, alkenyl substituted benzyl, alkynyl substituted benzyl, hydroxy substituted benzyl, alkoxy substituted benzyl, halogen substituted benzyl, aryl, —(CH$_2$)$_n$COOR$_5$ where n is 1 to 5 inclusive and R5 is any one of H, alkyl, alkenyl, alkynyl, halogen substituted alkanoate, N-tert-butoxy carbonyl (t-BOC), benzyl, alkyl substituted benzyl, alkenyl substituted benzyl, alkynyl substituted benzyl, hydroxy substituted benzyl, halogen substituted benzyl, —SO$_2$Ph, —SO$_2$-alkane, —SO$_2$-alkene, —SO$_2$-alkyne, —S—Ph, Ph—S—alkyl-, Ph—S-alkenyl-, Ph—S-alkynyl-,

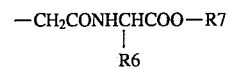

where R6 is any one of H, alkyl, benzyl, hydroxy substituted benzyl, indolyl-alkyl-, sulfhydryl-alkyl-, CH$_3$—S-alkyl-,

where R8 is H or methyl, imidazolyl-alkyl-, amide-alkyl-, -amine-alkyl- or

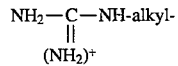

and R7 is H or alkyl,

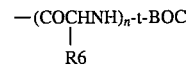

where n is 1 to 50 inclusive, or

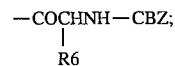

b) R1 is any one of H, alkyl, benzyl, hydroxy substituted benzyl, indolyl-alkyl-, sulfhydryl-alkyl-, CH$_3$—S-alkyl-,

imidazolyl-alkyl-, amide-alkyl-, amine-alkyl- or

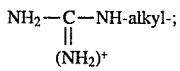

and either
1) Y is a non-steroidal anti-inflammatory compound, H, CBZ-(AA)$_n$ where n is 1 to 5 inclusive, preferably CBZ-L-Phe, CBZ-D-Phe, CBZ-L-Pro, CBZ-D-Pro, CBZ-L-Ala, or CBZ-Gly, N-t-BOC(AA)$_n$ where n is 1 to 5 inclusive, preferably any one of N-t-Boc-L-Phe, N-t-BOC-D-Phe, N-t-BOC-L-Pro, or N-t-BOC-D-Ala, OH, CN, Cl, F, Br, I, —SPh, alkyl, halogen substituted alkyl, alkenyl, halogen substituted alkenyl, alkynyl, Ph—SO—, halogen substituted alkynyl, —COO-alkane, —COO-alkene, —COO-alkyne, —CO—Ph, —PO(OCH$_3$)$_3$, Ph-alkyl-, Ph-alkenyl-, Ph-alkynyl-, —SO$_2$—Ph, —SO$_2$-alkane, —SO$_2$-alkene, —SO$_2$-alkyne, —S-alkane, —S-alkene, —S-alkyne, aryl or a heterocyclic group, preferably triazole or imidazole; or
2) Y is —O—CO—R3 where R3 is any one of H, alkyl, halogen substituted alkyl, alkenyl, halogen substituted alkenyl, alkynyl, halogen substituted alkynyl, Ph—S-alkyl-, Ph—S-alkenyl-, Ph—S-alkynyl-, Ph—SO$_2$-alkyl, Ph—SO$_2$-alkenyl-, or Ph—SO$_2$-alkynyl-; or
3) Y is represented by the following formula:

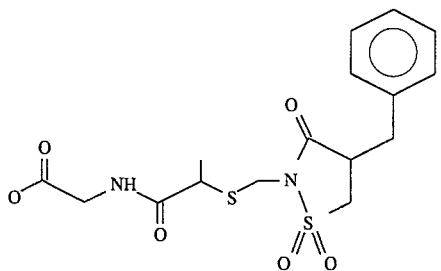

4) Y is

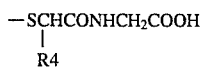

where R4 is alkyl, halogen substituted alkenyl, alkynyl, or halogen substituted alkynyl, c) and when R1 is benzyl and R2 is H, then Y cannot be F;
or a pharmaceutically acceptable salt thereof.

In another aspect, the invention features a compound represented by the following formula:

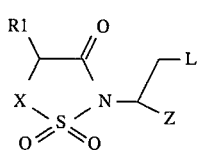

wherein:
a) X is CH2 or NR2 where R2 is any one of H, alkyl, halogen substituted alkyl, alkenyl, halogen substituted alkenyl, alkynyl, halogen substituted alkynyl, halogen substituted alkanoate, alkoxy, Ph-alkyl-, Ph-alkenyl-, Ph-alkynyl-, Ph-S-alkyl-, Ph-S-alkenyl-, Ph-S-alkynyl-, Ph—SO—, Ph—SO$_2$—, Ph—SO$_2$-alkyl-, Ph—SO$_2$-alkenyl-, PhSO$_2$-alkynyl-, benzyl, alkyl substituted benzyl, alkenyl substituted benzyl, alkynyl substituted benzyl, hydroxy substituted benzyl, alkoxy substituted benzyl, halogen substituted benzyl, aryl, —(CH$_2$)$_n$COOR5 where n is 1 to 5 inclusive and R5 is any one of H, alkyl, alkenyl, alkynyl, halogen substituted alkanoate, N-tert-butoxy carbonyl (t-BOC), benzyl, alkyl substituted benzyl, alkenyl substituted benzyl, alkynyl substituted benzyl, hydroxy substituted benzyl, halogen substituted benzyl, —SO$_2$Ph, —SO$_2$-alkane, SO$_2$-alkene, —SO$_2$-alkyne, —S—Ph, Ph—S-alkyl-, Ph—S-alkenyl-, Ph—S-alkynyl-,

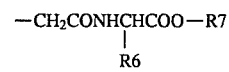

where R6 is any one of H, alkyl, benzyl, hydroxy substituted benzyl, indolyl-alkyl-, sulfhydryl-alkyl-, CH$_3$—S-alkyl-,

where R8 is H or methyl, imidazolyl-alkyl-, amide-alkyl-, amine-alkyl- or

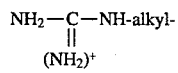

and R7 is H or alkyl

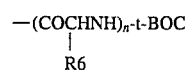

where n is 1 to 50 inclusive, or

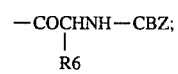

b) R1 is any one of H, alkyl, benzyl, hydroxy substituted benzyl, indolyl-alkyl-, sulfhydryl-alkyl-, CH$_3$—S-alkyl-,

imidazolyl-alkyl-, amide-alkyl-, amine-alkyl- or

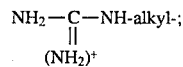

c) L is H, F, Cl, Br or I;
d) Z is H, F, Cl, Br, I, CN, benzyl, alkyl substituted benzyl, alkenyl substituted benzyl, alkynyl substituted benzyl, halogen substituted benzyl, —SO$_2$PH, —SO$_2$-alkane, —SO$_2$-alkene, —SO$_2$-alkyne, —S—Ph, Ph—S-alkyl-, Ph—S-alkenyl-, Ph—S-alkynyl-, or aryl;
or a pharmaceutically acceptable salt thereof.

In another aspect, the invention features a compound represented by the following formula:

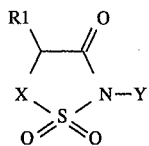

wherein:

a) X is CH2 or NR2 where R2 is any one of H, alkyl, halogen substituted alkyl, alkenyl, halogen substituted alkenyl, alkynyl, halogen substituted alkynyl, halogen substituted alkanoate, alkoxy, Ph-alkyl-, Ph-alkenyl-, Ph-alkynyl-, Ph—S-alkyl-, Ph—S-alkenyl-, Ph—S-alkynyl-, Ph—SO—, Ph—SO$_2$—, Ph—SO$_2$-alkyl, Ph—SO$_2$-alkenyl-, Ph—SO$_2$-alkynyl-, benzyl, alkyl substituted benzyl, alkenyl substituted benzyl, alkynyl substituted benzyl, hydroxy substituted benzyl, alkoxy substituted benzyl, halogen substituted benzyl, aryl, —(CH$_2$)$_n$COOR5 where n is 1 to 5 inclusive and R5 is any one of H, alkyl, alkenyl, alkynyl, halogen substituted alkanoate, N-tert-butoxy carbonyl (t-BOC), benzyl, alkyl substituted benzyl, alkenyl substituted benzyl, alkynyl substituted benzyl, hydroxy substituted benzyl, halogen substituted benzyl, —SO$_2$Ph, —SO$_2$-alkane, —SO$_2$-alkene, —SO$_2$-alkyne, —S—Ph, Ph—S-alkyl-, Ph—S-alkenyl-, Ph—S-alkynyl-,

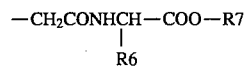

where R6 is any one of H, alkyl, benzyl, hydroxy substituted benzyl indolyl-alkyl-, sulfhydryl-alkyl-, CH$_3$—S-alkyl-,

where R8 is H or methyl, imidazolyl-alkyl-, amide-alkyl-, amine-alkyl- or

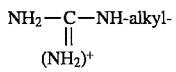

and R7 is H or alkyl,

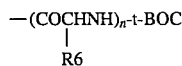

where n is 1 to 50 inclusive, or

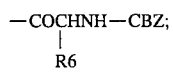

b) R1 is any one of H, alkyl, benzyl, hydroxy substituted benzyl, indolyl-alkyl-, sulfhydryl-alkyl-, CH$_3$—S-alkyl-,

imidazolyl-alkyl-, amide-alkyl-, amine-alkyl- or

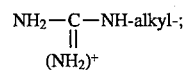

c) Y is H, —S—Ph, Ph—S-alkyl-, Ph—S-alkenyl-, Ph—S-alkynyl-, —SO$_2$Ph, —SO$_2$-alkane, —SO$_2$-alkene, —SO$_2$-alkyne or aryl;

or a pharmaceutically acceptable salt thereof.

In a related aspect, the invention features a method for reducing or preventing inflammation, preferably any one of tissue trauma, peritonitis, colitis, enteritis, vasculitis, pulmonary emphasema, chronic pulmonary infection, cystic fibrosis, bronchitis, arthritis, rheumatoid arthritis, psoriasis, allergic contact dermatitis, atopic dermatitis, glomerulonephritis, ARDS, pancreatitis or sepsis in a mammal, preferably a human, said method comprising administering a compound of the general formula:

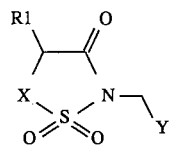

wherein:

a) X is CH2 or NR2 where R2 is any one of H, alkyl, halogen substituted alkyl, alkenyl, halogen substituted alkenyl, alkynyl, halogen substituted alkynyl, halogen substituted alkanoate, alkoxy, Ph-alkyl-, Ph-alkenyl-, Ph-alkynyl-, Ph—S-alkyl-, Ph—S-alkenyl-, Ph—S-alkynyl-, Ph—SO—, Ph—SO$_2$—, Ph—SO$_2$-alkyl-, Ph—SO$_2$-alkenyl-, Ph—SO$_2$-alkynyl, benzyl, alkyl substituted benzyl, alkenyl substituted benzyl, alkynyl substituted benzyl, hydroxy substituted benzyl, alkoxy substituted benzyl, halogen substituted benzyl, aryl, —(CH$_2$)$_n$COOR5 where n is 1 to 5 inclusive and R5 is any one of H, alkyl, alkenyl, alkynyl, halogen substituted alkanoate, N-tert-butoxy carbonyl (t-BOC), benzyl, alkyl substituted benzyl, alkenyl substituted benzyl, alkynyl substituted benzyl, hydroxy substituted benzyl, halogen substituted benzyl, —SO$_2$Ph, —SO$_2$-alkane, —SO$_2$-alkene, —SO$_2$-alkyne, —S—Ph, Ph—S-alkyl-, Ph—S-alkenyl-, Ph—S-alkynyl-,

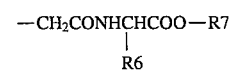

where R6 is any one of H, alkyl, benzyl, hydroxy substituted benzyl, indolyl-alkyl-, sulfhydryl-alkyl-, CH$_3$—S-alkyl-,

where R8 is H or methyl, imidazolyl-alkyl-, amide-alkyl-, -amine-alkyl- or

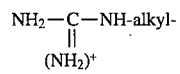

and R7 is H or alkyl,

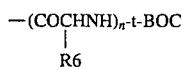

where n is 1 to 50 inclusive, or

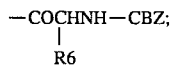

b) R1 is any one of H, alkyl, benzyl, hydroxy substituted benzyl, indolyl-alkyl-, sulfhydryl-alkyl-, CH$_3$—S-alkyl-,

imidazolyl-alkyl-, amide-alkyl-, amine-alkyl- or

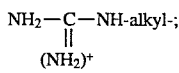

and either

1) Y is a non-steroidal anti-inflammatory compound, H, CBZ-(AA)$_n$ where n is 1 to 5 inclusive, preferably CBZ-L-Phe, CBZ-D-Phe, CBZ-L-Pro, CBZ-D-Pro, CBZ-L-Ala, or CBZ-Gly, N-t-BOC(AA)$_n$ where n is 1 to 5 inclusive, preferably any one of N-t-Boc-L-Phe, N-t-BOC-D-Phe, N-t-BOC-L-Pro, or N-t-BOC-D-Ala, OH, CN, Cl, F, Br, I, —SPh, alkyl, halogen substituted alkyl, alkenyl, halogen substituted alkenyl, alkynyl, Ph—SO—, halogen substituted alkynyl, —COO-alkane, —COO-alkene, —COO-alkyne, —CO—Ph, —PO(OCH$_3$)$_3$, Ph-alkyl-, Ph-alkenyl-, Ph-alkynyl-, —SO$_2$-Ph, —SO$_2$-alkane, —SO$_2$-alkene, —SO$_2$-alkyne, —S-alkane, —S-alkene, —S-alkyne, aryl or a heterocyclic group, preferably triazole or imidazole;

or

2) Y is —O—CO—R3 where R3 is any one of H, alkyl, halogen substituted alkyl, alkenyl, halogen substituted alkenyl, alkynyl, halogen substituted alkynyl, Ph—S-alkyl-, Ph—S-alkenyl-, Ph—S-alkynyl-, Ph—SO$_2$-alkyl-, Ph—SO$_2$-alkenyl-, or Ph—SO$_2$-alkynyl-;

or

3) Y is represented by the following formula:

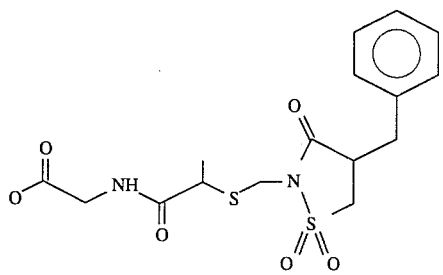

or

4) Y is

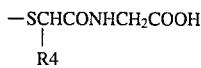

where R4 is alkyl, halogen substituted alkyl, alkenyl, halogen substituted alkenyl, alkynyl, or halogen substituted alkynyl;

c) and when R1 is benzyl and R2 is H, then Y cannot be F.

In a related aspect, the invention features a method for reducing or preventing inflammation, preferably any one of tissue trauma, peritonitis, colitis, enteritis, vasculitis, pulmonary emphasema, chronic pulmonary infection, cystic fibrosis, bronchitis, arthritis, rheumatoid arthritis, psoriasis, allergic contact dermatitis, atopic dermatitis, glomerulonephritis, ARDS, pancreatitis or sepsis in a mammal, preferably a human, said method comprising administering a compound of the general formula:

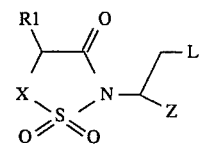

wherein:

a) X is CH2 or NR2 where R2 is any one of H, alkyl, halogen substituted alkyl, alkenyl, halogen substituted alkenyl, alkynyl, halogen substituted alkynyl, halogen substituted alkanoate, alkoxy, Ph-alkyl-, Ph-alkenyl-, Ph-alkynyl-, Ph—S-alkyl-, Ph—S-alkenyl-, Ph—S-alkynyl-, Ph—SO—, Ph—SO$_2$—, Ph—SO$_2$-alkyl-, Ph—SO$_2$-alkenyl-, PhSO$_2$-alkynyl-, benzyl, alkyl substituted benzyl, alkenyl substituted benzyl, alkynyl substituted benzyl, hydroxy substituted benzyl, alkoxy substituted benzyl, halogen substituted benzyl, aryl, —(CH$_2$)$_n$COOR5 where n is 1 to 5 inclusive and R5 is any one of H, alkyl, alkenyl, alkynyl, halogen substituted alkanoate, N-tert-butoxy carbonyl (t-BOC), benzyl, alkyl substituted benzyl, alkenyl substituted benzyl, alkynyl substituted benzyl, hydroxy substituted benzyl, halogen substituted benzyl, —SO$_2$Ph, —SO$_2$-alkane, —SO$_2$-alkene, —SO$_2$-alkyne, —S—Ph, Ph—S-alkyl-, Ph—S-alkenyl-, Ph—S-alkynyl-,

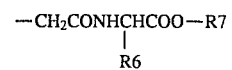

where R6 is any one of H, alkyl, benzyl, hydroxy substituted benzyl, indolyl-alkyl-, sulfhydryl-alkyl-, CH$_3$—S-alkyl-,

where R8 is H or methyl, imidazolyl-alkyl-, amide-alkyl-, amine-alkyl-, or

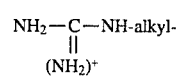

and R7 is H or alkyl,

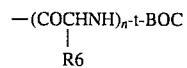

where n is 1 to 50 inclusive, or

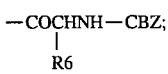

b) R1 is any one of H, alkyl, benzyl, hydroxy substituted benzyl, indolyl-alkyl-, sulfhydryl-alkyl-, $CH_3$—S-alkyl-,

imidazolyl-alkyl-, amide-alkyl-, amine-alkyl- or

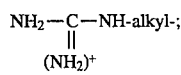

c) L is H, F, Cl, Br or I; and d) Z is H, F, Cl, Br, I, CN, benzyl, alkyl substituted benzyl, alkenyl substituted benzyl, alkynyl substituted benzyl, halogen substituted benzyl, —$SO_2PH$, —$SO_2$-alkane, —$SO_2$-alkene, —$SO_2$-alkyne, —S—Ph, Ph—S-alkyl-, Ph—S-alkenyl-, Ph—S-alkynyl-, or aryl.

In a related aspect, the invention features a method for reducing or preventing inflammation, preferably any one of tissue trauma, peritonitis, colitis, enteritis, vasculitis, pulmonary emphasema, chronic pulmonary infection, cystic fibrosis, bronchitis, arthritis, rheumatoid arthritis, psoriasis, allergic contact dermatitis, atopic dermatitis, glomerulonephritis, ARDS, pancreatitis or sepsis in a mammal, preferably a human, said method comprising administering a compound of the general formula:

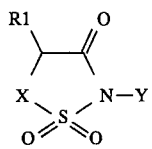

wherein:

a) X is CH2 or NR2 where R2 is any one of H, alkyl, halogen substituted alkyl, alkenyl, halogen substituted alkenyl, alkynyl, halogen substituted alkynyl, halogen substituted alkanoate, alkoxy, Ph-alkyl-, Ph-alkenyl-, Ph-alkynyl-, Ph—S-alkyl-, Ph—S-alkenyl-, Ph—S-alkynyl-, Ph—SO—, Ph—$SO_2$—, Ph—$SO_2$-alkyl, Ph—$SO_2$-alkenyl-, Ph—$SO_2$-alkynyl-, benzyl, alkyl substituted benzyl, alkenyl substituted benzyl, alkynyl substituted benzyl, hydroxy substituted benzyl, alkoxy substituted benzyl, halogen substituted benzyl, aryl, —$(CH_2)_n COOR5$ where n is 1 to 5 inclusive and R5 is any one of H, alkyl, alkenyl, alkynyl, halogen substituted alkanoate, N-tert-butoxy carbonyl (t-BOC), benzyl, alkyl substituted benzyl, alkenyl substituted benzyl, alkynyl substituted benzyl, hydroxy substituted benzyl, halogen substituted benzyl, —$SO_2Ph$, —$SO_2$-alkane, —$SO_2$-alkene, —$SO_2$-alkyne, —S—Ph, Ph—S-alkenyl-, Ph—S-alkynyl-,

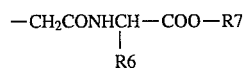

where R6 is any one of H, alkyl, benzyl, hydroxy substituted benzyl, indolyl-alkyl-, sulfhydryl-alkyl-, $CH_3$—S-alkyl-,

where R8 is H or methyl, imidazolyl-alkyl-, amide-alkyl-, amine-alkyl- or

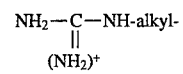

and R7 is H or alkyl,

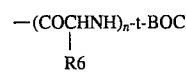

where n is 1 to 50 inclusive, or

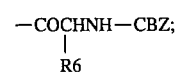

b) R1 is any one of H, alkyl, benzyl, hydroxy substituted benzyl, indolyl-alkyl-, sulfhydryl-alkyl-, $CH_3$—S-alkyl-,

imidazolyl-alkyl-, amide-alkyl-, amine-alkyl- or

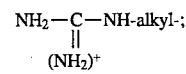

c) Y is H, —S—Ph, Ph—S-alkyl-, Ph—S-alkenyl-, Ph—S-alkynyl-, —$SO_2Ph$, —$SO_2$-alkane, —$SO_2$-alkene, —$SO_2$-alkyne or aryl.

In another aspect, the invention features a method for reducing or inhibiting the activity of a serine protease, preferably a serine protease produced by cancer cells capable of metastasis, more preferably a serine protease present in a cell or tissue extract, said method comprising:

contacting said serine protease with a compound of the general formula:

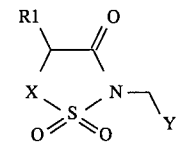

wherein:

a) X is CH2 or NR2 where R2 is any one of H, alkyl, halogen substituted alkyl, alkenyl, halogen substituted alkenyl, alkynyl, halogen substituted alkynyl, halogen substituted alkanoate, alkoxy, Ph-alkyl-, Ph-alkenyl-, Ph-alkynyl-, Ph—S-alkyl-, Ph—S-alkenyl-, Ph—S-alkynyl-, Ph—SO—, Ph—$SO_2$—, Ph—$SO_2$-alkyl-, Ph—$SO_2$-alkenyl-, Ph—$SO_2$-alkynyl-, benzyl, alkyl substituted benzyl, alkenyl substituted benzyl, alkynyl substituted benzyl, hydroxy substituted benzyl, alkoxy substituted benzyl, halogen substituted benzyl, aryl, —$(CH_2)_n COOR5$ where n is 1 to 5 inclusive and R5 is any one of H, alkyl, alkenyl, alkynyl, halogen substituted alkanoate, N-tert-butoxy carbonyl (t-BOC), benzyl, alkyl substituted benzyl, alkenyl substituted benzyl, alkynyl substituted benzyl, hydroxy substituted benzyl, halogen substituted benzyl, —SO$_2$Ph, —SO$_2$-alkane, —SO$_2$-alkene, —SO$_2$-alkyne, —S—Ph, Ph—S-alkyl-, Ph—S-alkenyl-, Ph—S-alkynyl-,

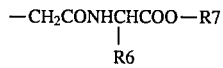

where R6 is any one of H, alkyl, benzyl, hydroxy substituted benzyl, indolyl-alkyl-,

where R8 is H or methyl, imidazolyl-alkyl-, amide-alkyl-, -amine-alkyl- or

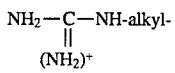

and R7 is H or alkyl,

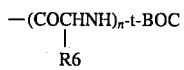

where n is 1 to 50 inclusive, or

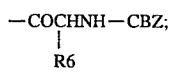

b) R1 is any one of H, alkyl, benzyl, hydroxy substituted benzyl, indolyl-alkyl-, sulfhydryl-alkyl-, CH$_3$—S-alkyl-,

imidazolyl-alkyl-, amide-alkyl-, amine-alkyl- or

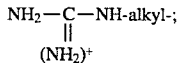

and either

1) Y is a non-steroidal anti-inflammatory compound, H, CBZ-(AA)$_n$ where n is 1 to 5 inclusive, preferably CBZ-L-Phe, CBZ-D-Phe, CBZ-L-Pro, CBZ-D-Pro, CBZ-L-Ala, or CBZ-Gly, N-t-BOC(AA)$_n$ where n is 1 to 5 inclusive, preferably any one of N-t-Boc-L-Phe, N-t-BOC-D-Phe, N-t-BOC-L-Pro, or N-t-BOC-D-Ala, OH, CN, Cl, F, Br, I, —SPh, alkyl, halogen substituted alkyl, alkenyl, halogen substituted alkenyl, alkynyl, Ph—SO—, halogen substituted alkynyl, —COO-alkane, —COO-alkene, —COO-alkyne, —CO—Ph, —PO(OCH$_3$)$_3$, Ph-alkyl-, Ph-alkenyl-, Ph-alkynyl-, —SO$_2$—Ph, —SO$_2$-alkane, —SO$_2$-alkene, —SO$_2$-alkyne, —S-alkane, —S-alkene, —S-alkyne, aryl or a heterocyclic group, preferably triazole or imidazole;

or

2) Y is —O—CO—R3 where R3 is any one of H, alkyl, halogen substituted alkyl, alkenyl, halogen substituted alkenyl, alkynyl, halogen substituted alkynyl, Ph—S-alkyl-, Ph—S-alkenyl-, Ph—S-alkynyl-, Ph—SO$_2$-alkyl-, Ph—SO$_2$-alkenyl-, or Ph—SO$_2$-alkynyl-;

or

3) Y is represented by the following formula:

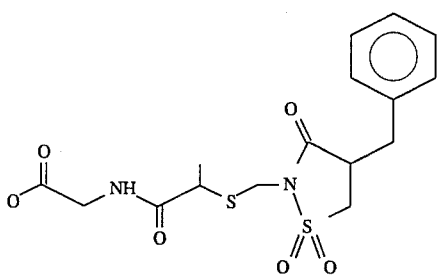

or

4) Y is

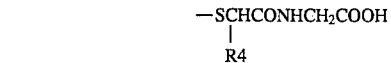

where R4 is alkyl, halogen substituted alkyl, alkenyl, halogen substituted alkenyl, alkynyl, or halogen substituted alkynyl;

c) and when R1 is benzyl and R2 is H, then Y cannot be F.

In a related aspect, the invention features a method for reducing or inhibiting the activity of a serine protease, preferably a serine protease produced by cancer cells capable of metastasis, more preferably a serine protease present in a cell or tissue extract, said method comprising:

contacting said serine protease with a compound of the general formula:

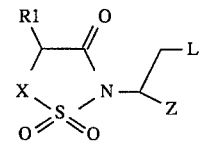

wherein:

a) X is CH2 or NR2 where R2 is any one of H, alkyl, halogen substituted alkyl, alkenyl, halogen substituted alkenyl, alkynyl, halogen substituted alkynyl, halogen substituted alkanoate, alkoxy, Ph-alkyl-, Ph-alkenyl-, Ph-alkynyl-, Ph—S—alkyl-, Ph—S-alkyl-, Ph—S-alkenyl-, Ph—S-alkynyl-, Ph—SO—, Ph—SO$_2$—, Ph—SO$_2$-alkyl-, substituted benzyl, alkenyl substituted benzyl, alkynyl substituted benzyl, hydroxy substituted benzyl, alkoxy substituted benzyl, halogen substituted benzyl, aryl, —(CH$_2$)$_n$COOR5 where n is 1 to 5 inclusive and R5 is any one of H, alkyl, alkenyl, alkynyl, halogen substituted alkanoate, N-tert-butoxy carbonyl (t-BOC), benzyl, alkyl substituted benzyl, alkenyl substituted benzyl, alkynyl substituted benzyl, hydroxy substituted benzyl, halogen substituted benzyl, —SO$_2$Ph, —SO$_2$-alkane, SO$_2$-alkene, —SO$_2$-alkyne, —S—Ph, Ph—S-alkyl, Ph—S-alkenyl-, Ph—S-alkynyl-,

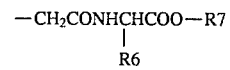

where R6 is any one of H, alkyl, benzyl, hydroxy substituted benzyl, indolyl-alkyl-, sulfhydryl-alkyl-, CH$_3$—S-alkyl-,

where R8 is H or methyl, imidazolyl-alkyl-, amide-alkyl-, amine-alkyl- or

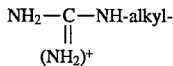

and R7 is H or alkyl,

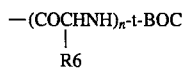

where n is 1 to 50 inclusive, or

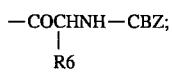

b) R1 is any one of H, alkyl, benzyl, hydroxy substituted benzyl, indolyl-alkyl-, sulfhydryl-alkyl-, $CH_3$—S-alkyl-,

imidazolyl-alkyl-, amide-alkyl-, amine-alkyl- or

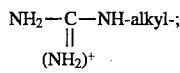

c) L is H, F, Cl, Br or I; and d) Z is H, F, Cl, Br, I, CN, benzyl, alkyl substituted benzyl, alkenyl substituted benzyl, alkynyl substituted benzyl, halogen substituted benzyl, —$SO_2$PH, —$SO_2$-alkane, —$SO_2$-alkene, —$SO_2$-alkyne, —S—Ph, Ph—S-alkyl-, Ph—S-alkenyl-, Ph—S-alkynyl-, or aryl.

In a related aspect, the invention features a method for reducing or inhibiting the activity of a serine protease, preferably a serine protease produced by cancer cells capable of metastasis, more preferably a serine protease present in a cell or tissue extract, said method comprising:

contacting said serine protease with a compound of the general formula:

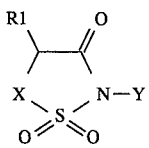

wherein:

a) X is CH2 or NR2 where R2 is any one of H, alkyl, halogen substituted alkyl, alkenyl, halogen substituted alkenyl, alkynyl, halogen substituted alkynyl, halogen substituted alkanoate, alkoxy, Ph-alkyl-, Ph-alkenyl-, Ph-alkynyl-, Ph—S-alkyl-, Ph—S-alkenyl-, Ph—S-alkynyl-, Ph—SO—, Ph—$SO_2$—, Ph—$SO_2$-alkyl, Ph—$SO_2$-alkenyl, Ph—$SO_2$-alkynyl-, benzyl, alkyl substituted benzyl, alkenyl substituted benzyl, alkynyl substituted benzyl, hydroxy substituted benzyl, alkoxy substituted benzyl, halogen substituted benzyl, aryl, —$(CH_2)_n$COOR5 where n is 1 to 5 inclusive and R5 is any one of H, alkyl, alkenyl, alkynyl, halogen substituted alkanoate, N-tert-butoxy carbonyl (t-BOC), benzyl, alkyl substituted benzyl, alkenyl substituted benzyl, alkynyl substituted benzyl, hydroxy substituted benzyl, halogen substituted benzyl, —$SO_2$Ph, —$SO_2$-alkane, —$SO_2$-alkene, —$SO_2$-alkyne, —S—Ph, Ph—S-alkyl-, Ph—S-alkenyl-, Ph—S-alkynyl-,

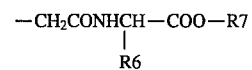

where R6 is any one of H, alkyl, benzyl, hydroxy substituted benzyl, indolyl-alkyl-, sulfhydryl-alkyl-, $CH_3$—S-alkyl-,

where R8 is H or methyl, imidazolyl-alkyl-, amide-alkyl-, amine-alkyl- or

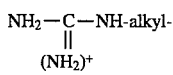

and R7 is H or alkyl,

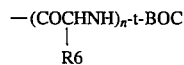

where n is 1 to 50 inclusive, or

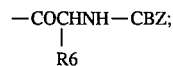

b) R1 is any one of H, alkyl, benzyl, hydroxy substituted benzyl, indolyl-alkyl-, sulfhydryl-alkyl-, $CH_3$—S-alkyl-,

imidazolyl-alkyl-, amide-alkyl-, amine-alkyl- or

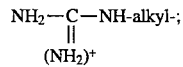

c) Y is H, —S—Ph, Ph—S-alkyl-, Ph—S-alkenyl-, Ph—S-alkynyl-, —$SO_2$Ph, —$SO_2$-alkane, —$SO_2$-alkene, —$SO_2$-alkyne or aryl.

An alkane or alkyl, as used herein, is a branched or straight chain lower hydrocarbon of 1 to 5 (inclusive) carbon atoms. Preferred alkyls include methyl, ethyl, propyl, n-butyl and isobutyl. A halogen, as used herein, is F, Cl, Br, or I. A halogen substituted alkyl, as used herein, is an alkyl with at least one halogen. An alkene or alkenyl, as used herein, is a branched or straight chain lower hydrocarbon of 1 to 5 (inclusive) carbon atoms and at least 1 carbon-carbon double bond. A halogen substituted alkenyl, is an alkenyl with at least one halogen. An alkyne or alkynyl, as used herein, is a branched or straight chain lower hydrocarbon of 1 to 5 (inclusive) carbon atoms and at least one carbon-carbon triple bond. A halogen substituted alkynyl, as used herein, is an alkynyl substituted with at least one halogen. An alkanoate, as used herein, is an ester of the formula —$(CH_2)_n$COO-alkane, where n is 1 to 3 (inclusive). A halogen substituted alkanoate, as used herein, is an alkanoate with at least one halogen. Preferred halogen substituted alkanoates include —$CH_2COOCH_2Cl$ and —CH(Cl)COOCH$_3$. An alkoxy, as used herein, is 1 to 5 carbon atoms (inclusive), preferably methoxy, ethoxy, propoxy, n-butoxy, and iso-butoxy. A Ph, as used herein, is a phenyl. Preferably a phenyl is substituted with an alkyl, alkoxy, hydroxy, or halogen, each alone or in combination with at least one other alkyl, alkoxy, hydroxy, or halogen. Preferred substituted phenyls include fluorophenyl, chlorophenyl, bromophenyl, iodophenyl, dichlorophenyl, triiodophenyl, fluorochlorophenyl, flourobromophenyl, dimethylphenyl fluorochlorobromophenyl, methoxyphenyl, dimethoxyphenyl, hydroxyphenyl, and fluoromethoxyphenyl. N-t-BOC(AA)$_n$, as used herein, is a t-butyloxycarbonyl group linked to 1 to 5 (inclusive) amino acids. Preferred examples include N-t-Boc-L-Phe, N-t-BOC-D-Phe, N-t-BOC-L-Pro, N-t-BOC-D-Ala, N-t-BOC-Ala-Gly-Gly, N-t-BOC-Gly-Pro. CBZ-(AA)$_n$, as used herein, is a N-carbobenzoxy group linked to 1 to 5 (inclusive) amino acids. Preferred examples include CBZ-L-Phe, CBZ-D-Phe, CBZ-L-Pro, CBZ-D-Pro, CBZ-L-Ala, CBZ-Gly, CBZ-Ala-Glu, or CBZ-Ala-Gly-Gly. A heterocyclic group, as used herein, is a five or six membered carbon ring with at least one nitrogen atom. Preferred heterocyclic groups include triazolyl, imidazolyl, pyrazolyl, pyridyl, pyrazinyl, pyrimidinyl, pyridazinyl, indolizinyl, or isoindolyl. An aryl, as used herein, can be 6 to 40 carbons (inclusive), preferably 6 to 20 carbons (inclusive), and can be a mono- or poly-cyclic hydrocarbon ring. Preferred aryls include tolyl, cumyl, or napthyl. Preferably, an aryl is substituted with at least one halogen, alkyl, hydroxy, alkoxy or carboxy group, each substitution alone or in combination with at least one halogen, alkyl, hydroxy, alkoxy or carboxy group. A nonsteroidal anti-inflammatory compound, as used herein, is any one of ibuprofen, diclofenac, fenoprofen, naproxen, ketoprofen, aspirin, 5-ASA, or derivatives thereof. A vinyl, as used herein, is —CH=CH$_2$. A t-styryl, as used herein, is —CH=CHC$_6$H$_5$. A t-cinnamyl, as used herein, is —CH$_2$CH=CHC$_6$H$_5$. A Bzl, as used herein, is a benzyl group.

Pharmaceutically acceptable salts, as defined herein, are inorganic acid addition salts such as hydrochloride, sulfate, and phosphate, and organic acid addition salts such as acetate, maleate, fumarate, tartrate, and citrate. Examples of the pharmaceutically acceptable metal salts are alkali metal salts such as sodium salt and potassium salt, alkaline earth metal salts such as magnesium salt and calcium salt, aluminum salt, and zinc salt. Examples of the pharmaceutically acceptable ammonium salts are ammonium salt and tetramethyl ammonium salt. Examples of the pharmaceutically acceptable organic amine addition salts are salts with morpholine and piperidine. Examples of the pharmaceutically acceptable amino acid addition salts are salts with lysine, glycine, and phenylalanine.

Inflammation, as used herein, is any pathological process involving reactions (e.g. unmodulated serine protease activity or neutrophil diapedesis), that occur in affected blood vessels and adjacent tissues in response to injury or abnormal stimulation by a physical, chemical or biological agent. Preferred examples of inflammation include tissue trauma, peritonitis, colitis, enteritis, vasculitis, pulmonary emphasema, chronic pulmonary infection, cystic fibrosis, bronchitis, arthritis, rheumatoid arthritis, psoriasis, allergic contact dermatitis, atopic dermatitis, glomerulonephritis, ARDS (Adult respiratory distress syndrome), pancreatitis and sepsis.

DESCRIPTION OF PREFERRED EMBODIMENTS

The drawings are described first.

Figure 3:
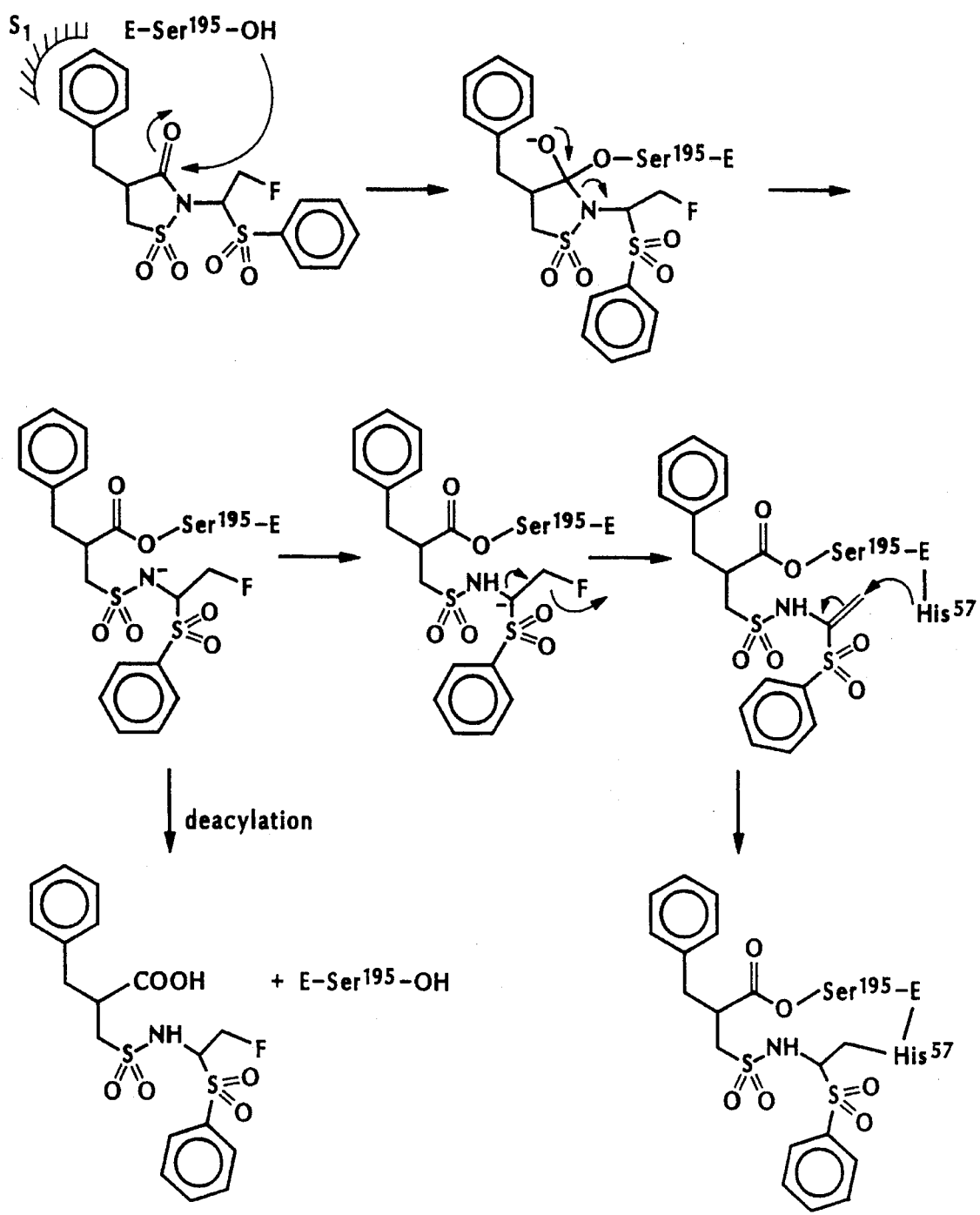

FIG. 3 is drawing outlining the postulated mechanism by which a isothiazolidin-3-one 1,1 dioxide derivative inactivates the serine protease Cath G. Ser$^{195}$ and His$^{57}$ each refer to active site amino acid residues. Both Ser$^{195}$ and His$^{57}$ are covalently bound to the derivative, forming an inactive enzyme complex. Compound 1 is shown in this example.

Figure 4:
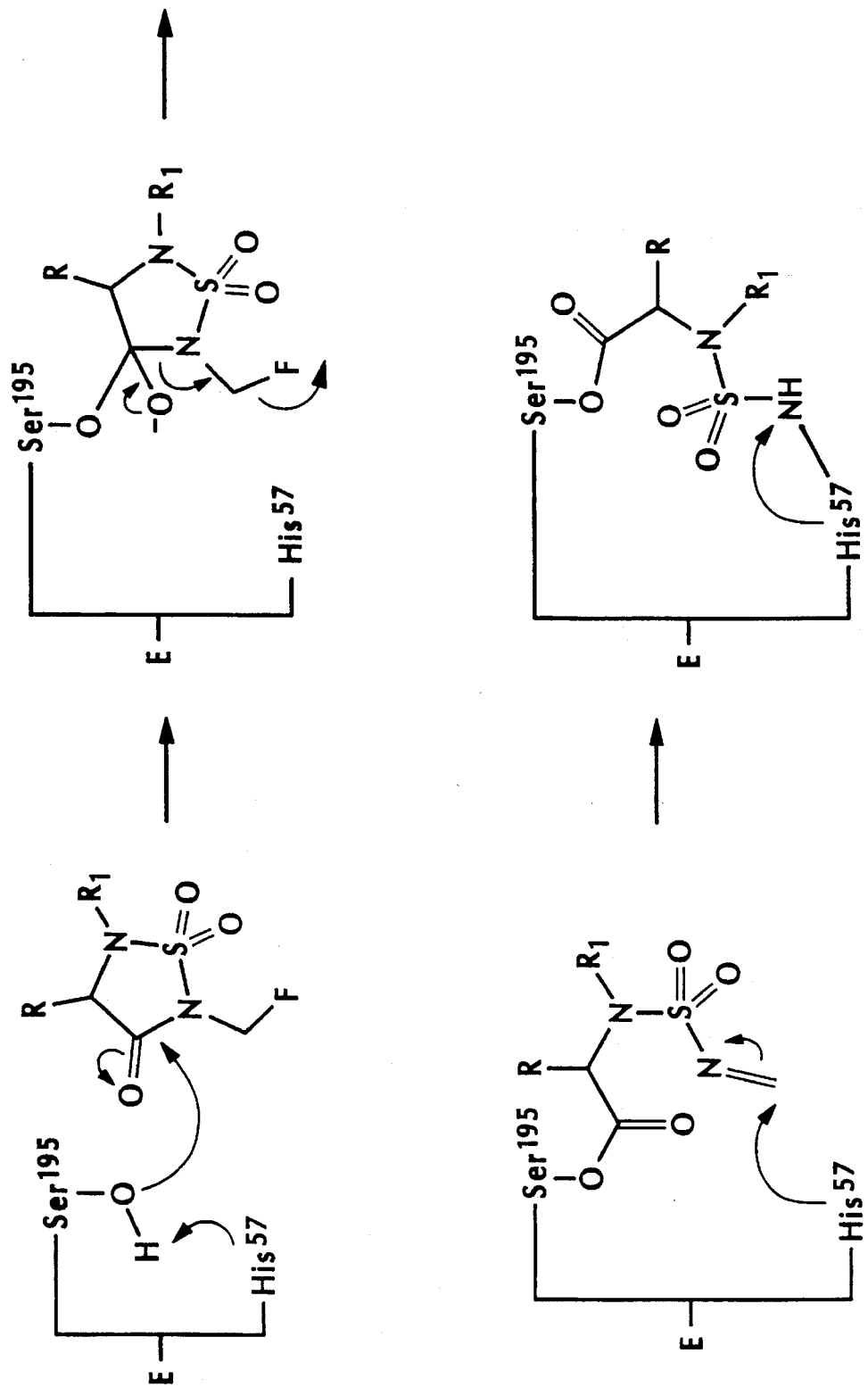

FIG. 4 is a drawing outlining the postulated mechanism by which a 3-oxo-1,2,5-thiadiazolidine 1,1-dioxide derivative inhibits the serine protease Cath G. Ser$^{195}$ and His$^{57}$ each refer to active site amino acid residues. Both Ser$^{195}$ and His$^{57}$ are covalently bound to the derivative, forming an inactive enzyme complex.

Figure 5:
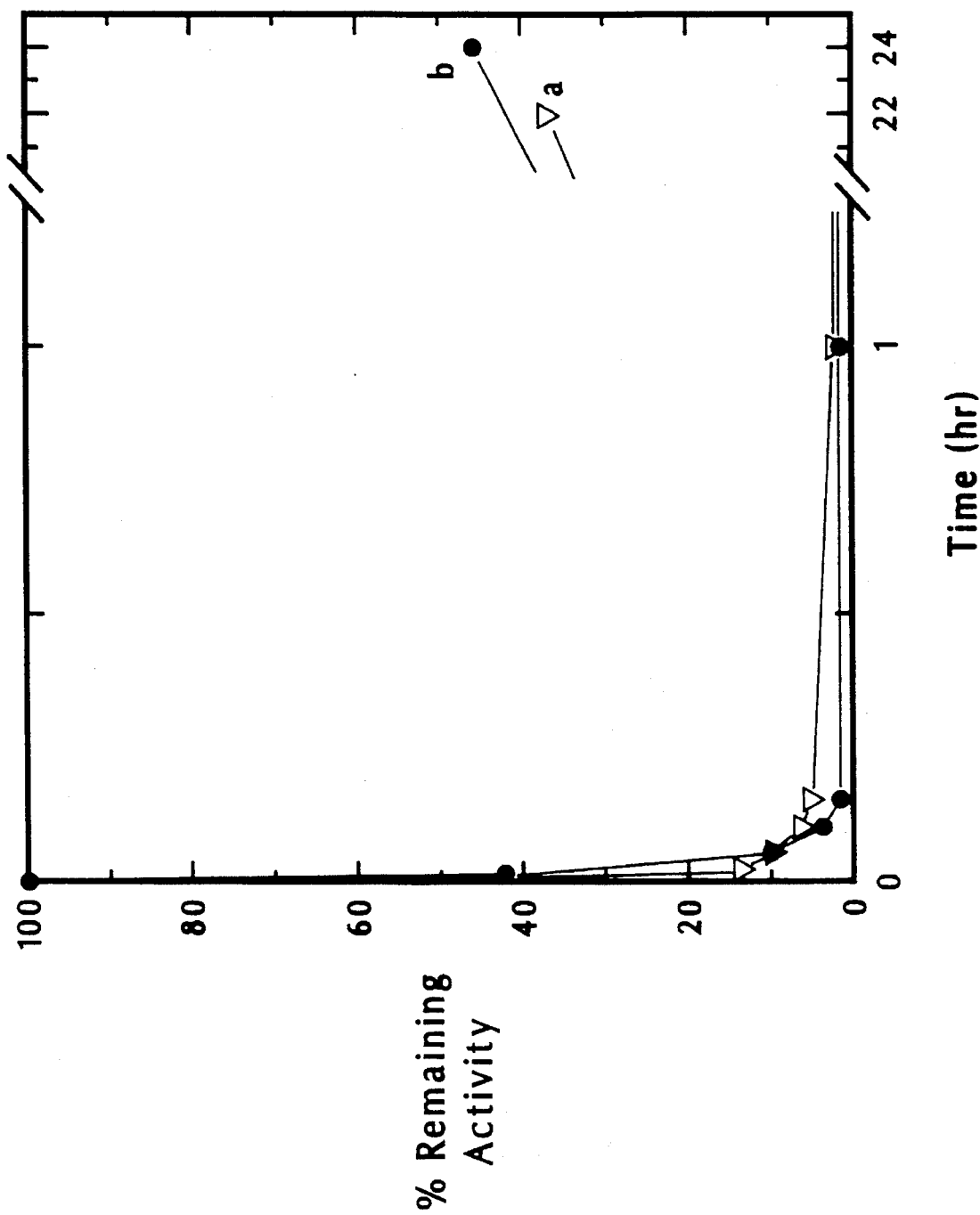

FIG. 5 is a graph depicting the time-dependent loss of serine protease activity after incubation with an isothiazolidin-3-one 1,1 dioxide derivative. Human leukocyte cathepsin G (1.33 uM) is incubated with compound 8 (133 uM) (a) or compound 10 (13.3 uM) (b) in 0.1M HEPES buffer, pH 7.5, and 10% DMSO. Aliquots were withdrawn at different time intervals and assayed for enzymatic activity using methoxysuccinyl Ala-Ala-Pro-Phe p-nitroanilide.

Figure 6:
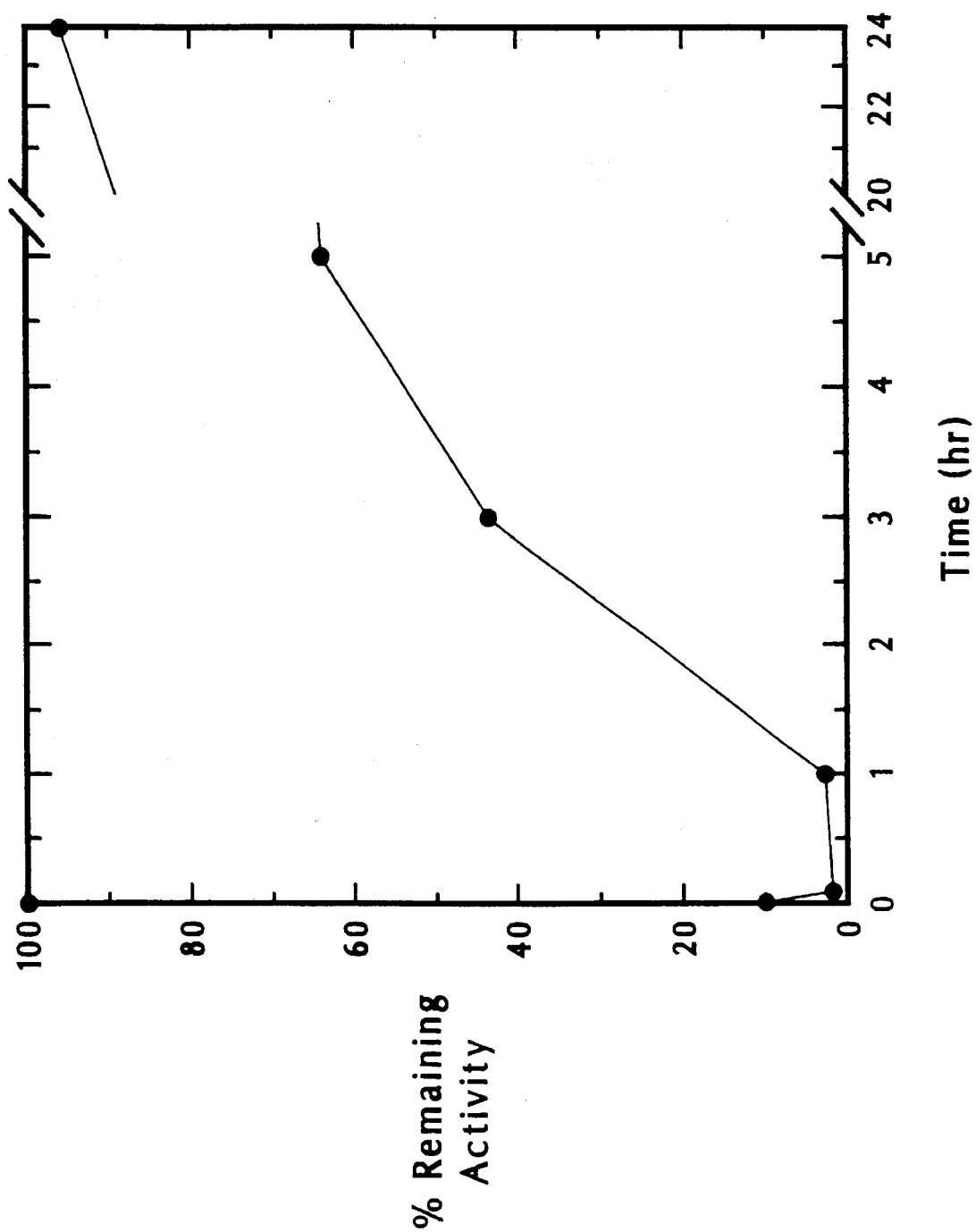
Figure 7B:
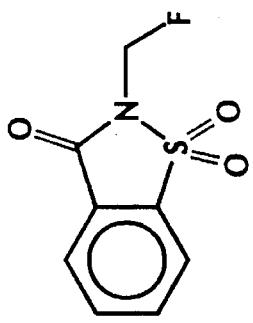
Figure 7D:
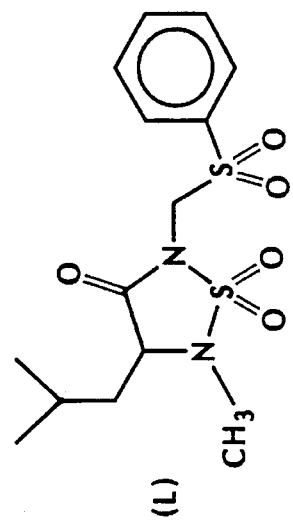
Figure 7A:
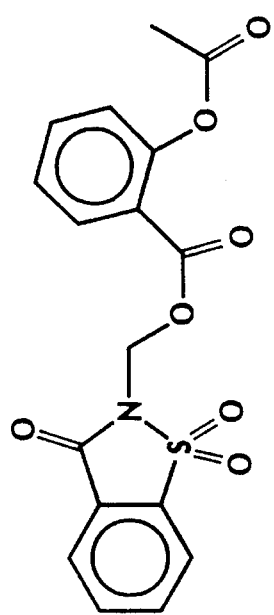
Figure 7C:
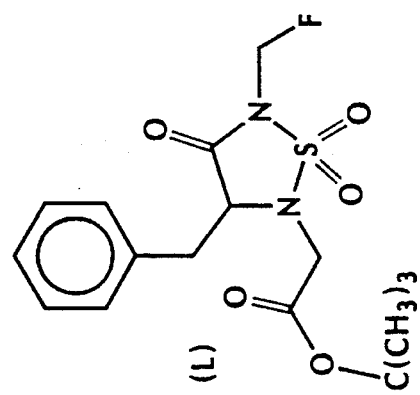

FIG. 6 is a graph depicting the time-dependent loss of serine protease activity after incubation with a 3-oxo-1,2,5-thiadiazolidine 1,1-dioxide derivative. Human leukocyte cathepsin G (1.48 µM was incubated with inhibitor 5A (1.48 µM in 0.1M HEPES buffer, pH 7.5, and 1% DMSO. Aliquots were withdrawn at different time intervals and assayed for enzymatic activity using methoxysuccinyl Ala-Ala-Pro-Phe p-nitroanilide.

FIGS. 7A, 7B, 7C, and 7D are drawings of compounds screened for capacity to inhibit experimentally induced rat peritonitis in vivo. Compounds 7A and 7B have been disclosed elsewhere (Groutas, W. C. et al. *J. Med. Chem.* 36, 3178 (1993)). Compounds 4a (7C) and 3e (7D) are 3-oxo-1,2,5-thiadiazolidine 1,1-dioxide derivatives of the invention.

Figure 8:
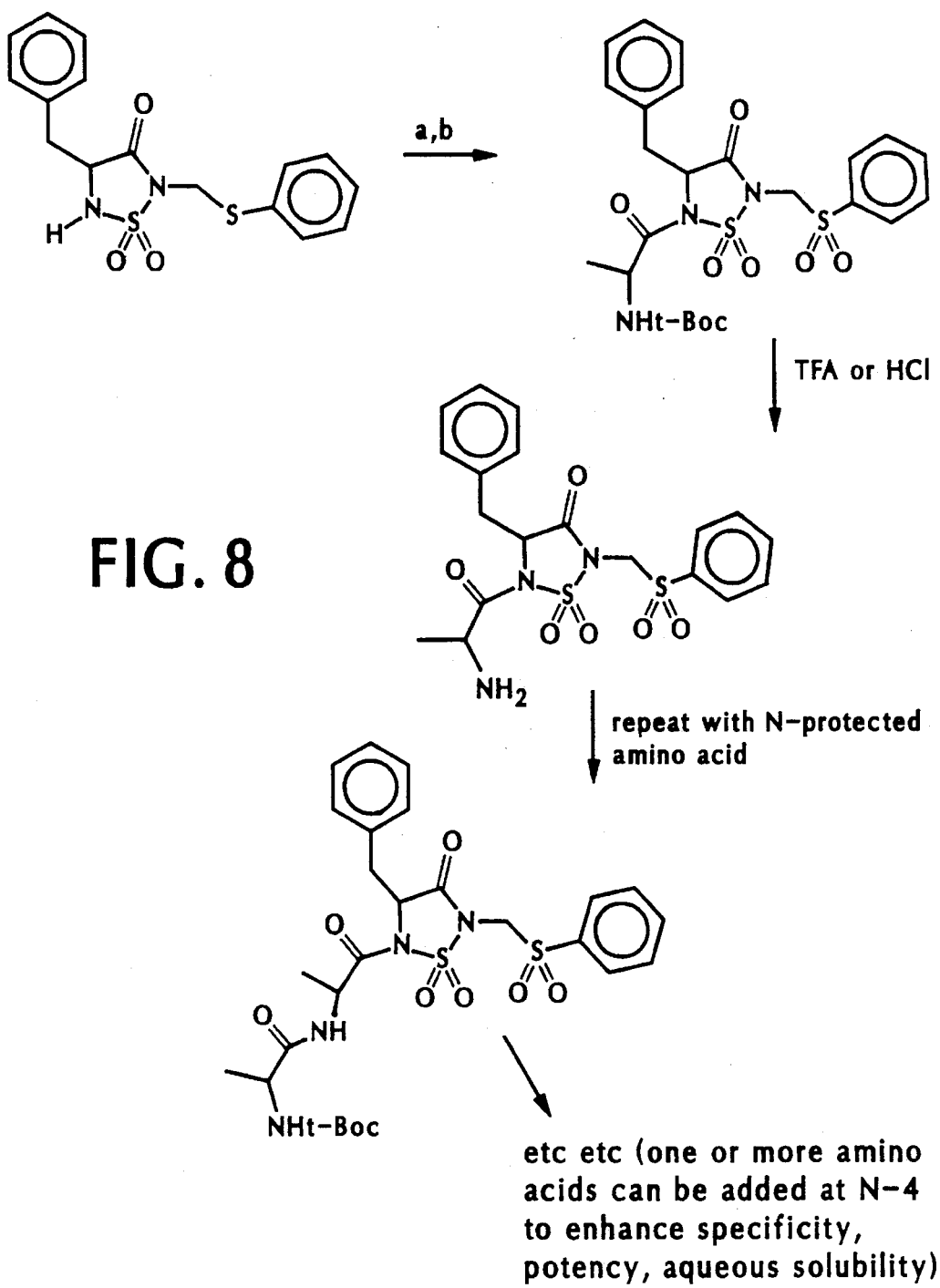

FIG. 8 is a drawing outlining the chemical synthesis of 3-oxo-1,2,5-thiadiazolidine 1,1-dioxide derivatives comprising 1 or more N-protected amino acids at the N4 position.

I. Preparation of Compounds 1–10 (FIG. 1)

Figure 1:
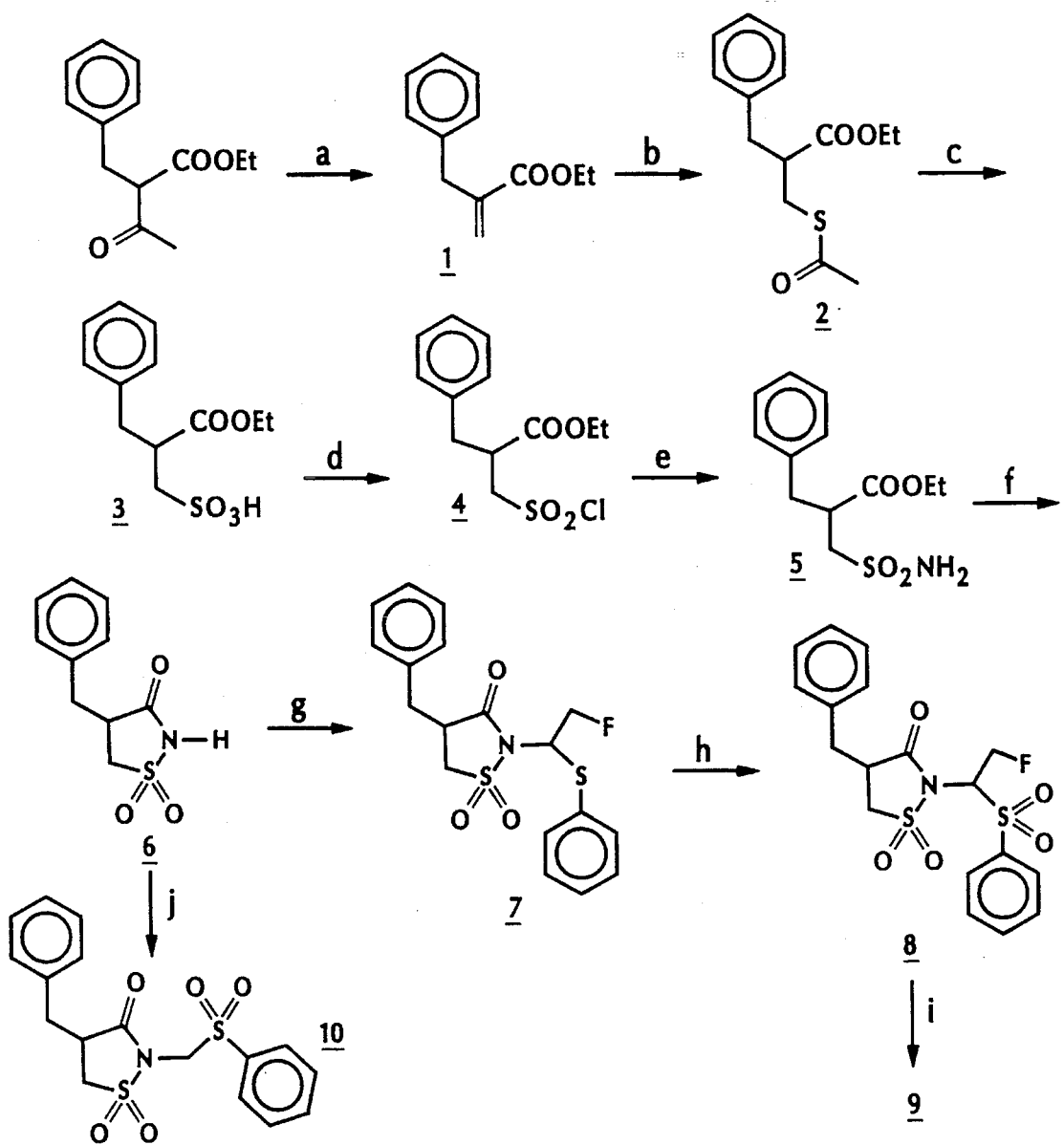
FIG. 1 is a drawing of the chemical synthesis of isothiazolidin-3-one 1,1 dioxide derivatives. Script below the drawing refers to reagents used to obtain the desired chemical reaction or purification step.

Compounds 7–9 were synthesized as illustrated in FIG. 1. Compound 1 (2-benzyl ethyl acrylate) was synthesized essentially as described in the literature (Ueno et al., *Tetrahedron Lett.*, 1978). The NMR and IR spectra of the synthesized compounds were recorded on a Perkin Elmer 1330 infrared spectrophotometer and a Varian XL 300 NMR spectrometer, and were consistent with the assigned structures. Elementary analyses were performed by M-H-W Laboratories, Phoenix, Ariz.

i) Synthesis of Compound 2

Ethyl 2-benzyl acrylate 1 (5.14 g; 27 mmol) and thioacetic acid (3.73 g; 47 mmol) were mixed and kept at room temperature for a week. The reaction mixture was diluted with ethyl ether (20 mL) and extracted with 5% aqueous sodium bicarbonate (5×30 mL). The organic layer was dried over anhydrous sodium filtrate, filtered and evaporated yielding 2 as a yellow oil (6.47 g; 90% yield). $^1$H NMR: δ 1.15(t,3H), 2.31(s,3H), 2.85–3.17 (m,5H), 4.06(q,2H), 7.12–7.30(m,5H).

ii) Synthesis of Compound 4 (3-Phenyl-(2-Carboethoxy)propanesulfonyl Chloride)

Compound 2 (2.66 g; 10 mmol) was added to a solution of performic acid (prepared by mixing 6.8 mL 30% hydrogen peroxide and 34 mL formic acid) at 0° C. The reaction mixture was stirred overnight, poured into 30 mL of water and extracted with carbon tetrachloride (2×30 mL). The aqueous layer was separated and evaporated in vacuo, leaving an oily product 3 that was used in the preparation of 4 without further purification.

Compound 3 (7.0 g; 25 mmol) was mixed with phosphorous trichloride (8.48 g; 62.5 mmol) and refluxed for 1 h. Excess reagent was removed under reduced pressure and the residue was dissolved in methylene chloride (100 mL) and filtered through a silica gel pad. Removal of the solvent in vacuo yielded 4. $^1$H NMR: $\delta$ 1.22 (t, 3H), 2.92 (dd, 1H), 3.15(dd, 1H), 3.43(m, 1H), 3.68(dd,1H), 4.20(m,3H), 7.15–7.40 (m, 5H) .

iii) Synthesis of Compound 5 (3-Phenyl-(2-carboethoxy)propanesulfonamide)

To 3-Phenyl-(2-carboethoxy)propanesulfonyl chloride 4 (2.0 g; 6.9 mmol) in dry THF (3 mL) was added dropwise 15N ammonium hydroxide (1.38 mL) with stirring while maintaining the temperature between 0°–5° C. Stirring was continued for 0.5 h at room temperature after the addition was completed. The solvent was removed in vacuo and the residue was dissolved in ether (15 mL) and washed with water (10 Ml) and brine (2×10 mL). The organic layer was separated, dried and evaporated, yielding a pure product, mp 67°–8° C. (1.23 g; 67% yield). $^1$H NMR: $\delta$ (1.15(t,3H), 2.88–3.07(m,2H), 3.17–3.32(m,2H), 3.62(dd, 1H), 4.10(q, 2H), 5.25(bs,2H), 7.13–7.20(m,5H).

iv) Synthesis of Compound 6 (4-Benzylisothiazolinin-3-one 1,1-dioxide)

A solution of compound 5 (1.35 g; 5 mmol) in 10 mL THF was carefully added to a suspension of sodium hydride (0.22 g; 5.5 mmol) in 15 mL dry THF kept at −15° C. The mixture was allowed to warm up to room temperature and stirred overnight. The resulting solid was collected and washed with ethyl ether. The solid was then dissolved in methanol (20 mL) and stirred with Dowex-H$^+$ resin for 0.5 h. The resin was filtered off and washed with methanol (20 mL). The filtrate was concentrated in vacuo, leaving behind compound 6 as a white solid, mp 115°–6° C. (0.87 g; 78% yield). $^1$H NMR: $\delta$ 2.9(m, 1H), 3.35–3.65(m,4H), 7.15–7.4(m,5H), 8.8(s,1H).

v) Synthesis of Compound 7 (4-Benzyl-2-(2-fluoro-1-phenylthioethyl) isothiazolidin-3-one 1,1-dioxide)

A solution of N-chlorosuccinimide (1.1 g; 8.25 mmol) and phenyl-(2-fluoroethyl)sulfide (1.28 g; 8.25 mmol) in 25 mL methylene chloride was stirred for 0.5 h at room temperature. Methylene chloride (25 mL) was added to the reaction mixture and washed with water (2×35 mL). The organic layer was dried and evaporated to yield 1.48 g phenyl-(1-chloro-2-fluoroethyl)sulfide as an oily material which was mixed with 6 (2.23 g; 9.9 mmol), triethylamine (1.0 g; 9.9 mmol) and dry acetonitrile (30 mL) and refluxed for 5 h. The solvent was removed in vacuo and the residue was dissolved in methylene chloride (75 mL) and washed with water (50 mL), 5% aqueous sodium bicarbonate (50 mL) and 5% hydrochloric acid (50 mL). The organic layer was dried over anhydrous sodium sulfate and the solvent removed, leaving a crude product (2.78 g). The crude product was purified by flash chromatography using hexane/methylene chloride as the eluting solvent, mp 73°–74° C. (1.92 g; 62% yield). $^1$H NMR: $\delta$ 2.80–2.98(m, 1H), 3.2–3.45(m,4H), 4.6–4.8(m, 1H), 4.82–5.10(m, 1H), 5.45(m, 1H), 7.1–7.35(m,3H), 7.5–7.65(m,2H).

vi) Synthesis of Compound 8 (4-Benzyl-2-(2-fluoro-1-phenylsulfonylethyl) isothiazolidin-3-one 1,1-dioxide)

Compound 7 (0.57 g; 1.5 mmol) in 10 mL methylene chloride was treated with m-chloroperbenzoic acid (0.86 g; 3.3 mmol) at 0° C. and stirred overnight at room temperature. The solvent was removed in vacuo and the residue was triturated with ethyl ether (50 mL). The undissolved solid was filtered off, washed with ethyl ether (2×10 mL) and dried, yielding 0.42 g (70% yield) of compound 8, mp 169°–170° C. $^1$NMR: $\delta$ 2.9–3.05(m, 1H), 3.45–3.65(m,4H), 5.2–5.6(m,3H), 7.23–7.4(m,5H), 7.68(m,2H), 7.8(m, 1H), 8.05(m,2H).

vii) Synthesis of Compound 9 (4-Benzyl-2-(1-phenylsulfonylvinyl)isothiazolidin-3-one 1,1-dioxide)

Compound 8 (0.55 g; 1.34 mmol) in 30 mL methylene chloride was stirred at room temperature with 20 g silica gel (Merck, grade 60, 230–400) overnight. The silica gel was filtered off and washed with several portions of methylene chloride. Evaporation of the solvent afforded compound 9, mp 53°–4° C. (0.35 g; 67% yield). $^1$H NMR: $\delta$ 3.0(m, 1H), 3.3–3.41(m,2H), 3.6(m,2H), 6.26(d,1H), 6.8(d, 1H), 7.15–7.40(m,5H), 7.5–7.7 (m, 3H), 7.9 (m, 2H).

viii) Synthesis of Compound 10 (4-Benzyl-2-(1-phenylsulfonylmethyl)isothiazolidin-3-one 1,1-dioxide)

A mixture of 4-benzylisothiazolidin-3-one 1,1-dioxide 4 (0.9 g; 4 mmol), chloromethyl phenyl sulfide (0.63 g; 4 mmol) and triethylamine (0.40 g; 4 mmol) in dry acetonitrile (10 mL) was refluxed for 2 h. The solvent was removed in vacuo and the residue was dissolved in methylene chloride and extracted with water (50 mL) 5% hydrochloric acid (50 mL) and 5% sodium bicarbonate (50 mL). The organic layer was dried and evaporated, leaving a crude product (0.8 g) which was purified by flash chromatography (silica gel/ hexane:methylene chloride), yielding 0.32 g of 4-benzyl-2-(1-Phenylthiomethyl)isothiazolidin-3-one 1,1-dioxide. This was oxidized to compound 10 by stirring overnight with m-chloroperbenzoic acid (2.2 eq) in methylene chloride. Compound 10 was obtained by evaporating off the solvent, adding ether and collecting the precipitated product, mp 137°–8° C. (0.38 g; 90% yield). $^1$H NMR: $\delta$ 2.85(m, 1H), 3.3(m,2H), 3.5(m,2H), 4.87(s,2H), 7.15(dd,2H), 74.0–7.25(m,3H), 7.81–7.70(m,3H), 8.0(m,2H).

Those skilled in the art will appreciate that the starting reagent in FIG. 1 may be any suitable 2-substituted acrylate ester in order to vary the side group at the number 4 position of the ring. Preferred 2-substituted acrylate esters include 2-lower alkyl- and 2-lower alkyl aryl ethyl acrylates, most preferably 2-benzyl ethyl acrylate.

Figure 2:
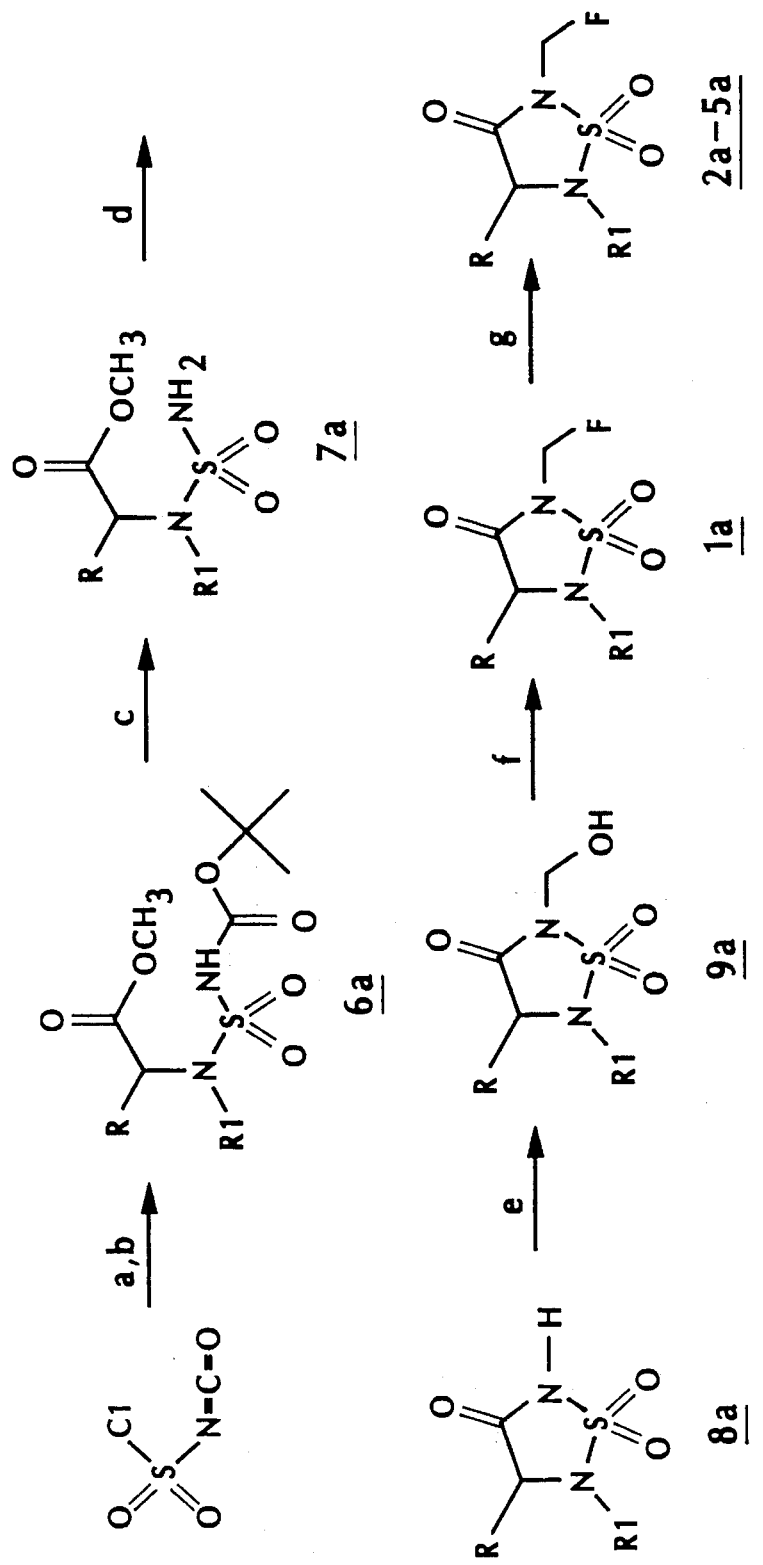
FIG. 2 is a drawing of the chemical synthesis of 3-oxo-1,2,5-thiadiazolidine 1,1-dioxide derivatives. Script below the drawing refers to reagents used to obtain the desired chemical reaction.

II. Preparation of Compounds 1a–5a (FIG. 2).

The synthesis of a 3-oxo-1,2,5-thiazolidine-1,1 dioxide ring has been described (Auf, N. et al. *Tetrahedron Lett.* 32, 6545–6546, (1991); Lee, C-H, et al. *J. Org. Chem.* 54, 3077–3083 (1989)). Compounds 1a–5a were synthesized as shown in FIG. 2. The NMR and IR spectra of the synthesized compounds were recorded on a Varian XL-300 NMR spectrometer and a Perkin-Elmer infrared spectrophotometer, respectively, and were consistent with the assigned structures. Elemental analyses were performed by M-H-W Laboratories, Phoenix, Ariz.

i) Synthesis of Compound 6a ((S)-Methyl-2—(tert-butoxycarbonylsulfamido) 3-Phenyl propanoate)

A solution of 10.5 g (75 mmol) of chlorosulfonyl isocyanate in 150 mL of dry methylene chloride was cooled in an ice bath under a nitrogen atmosphere and a solution of dry t-butyl alcohol (5.48 g; 74 mmol) in 75 mL methylene chloride was added dropwise. The resulting solution was added dropwise to a mixture of L-Phenylalanine methyl ester hydrochloride salt (16.1 g; 74 mmol) and triethylamine (15.0 g; 148 mmol) in 150 mL methylene chloride kept at 0°

C. The reaction mixture was allowed to warm to room temperature and stirred for two additional hours. The salt was filtered off and the filtrate was washed sequentially with water (2×30 mL) and brine (2×30 mL), and dried over anhydrous sodium sulfate. Removal of the solvent gave compound 6a (25.6 g; 96% yield) as a white solid, mp 120°–1° C. $^1$H NMR (CDCl$_3$): δ 7.48 (s,1H), 7.4–7.1 (m,5H), 5.72 (d, 1H), 4.52 (m, 1H), 3.71 (s,3H), 3.13 (d,2H), 1.47 (s,9H); [α]$_D$+46.9 (Cl, CH$_2$Cl$_2$). Anal. Calcd. for C$_{15}$H$_{22}$N$_2$O$_6$S. C, 50.26; H, 6.19; N, 7.82. Found: C, 50.16; H, 7.45; N, 8.76.

ii) Synthesis of Compound 7a (S)-Methyl 2-sulfamido-3-Phenylpropanoate)

Compound 7a (10.5 g; 29 mmol) was treated with trifluoroacetic acid (32 mL) in 8 mL of methylene chloride and stirred for 2 h at room temperature. The solvent and excess trifluoroacetic acid were removed in vacuo; leaving an oily residue that was taken up in methylene chloride (50 mL) and washed with 5% aqueous sodium bicarbonate (2×30 mL), brine (2×30 mL) and dried. Removal of the solvent left 7a as an oily product (7.2 g; 96% yield). $^1$H NMR (CDCl$_3$): δ 7.37–7.15 (m,5H), 4.74 (s,2H), 4.38 (m, 1H), 3.37 (s,3H), 3.2–3.0 (m,2H); [α]$_D$+10.85. Calcd. for C$_{10}$H$_{14}$N$_2$O$_4$: C, 46.50; H, 5.46; N, 10.85. Found: C, 46.41; H, 5.55; N, 10.70.

iii) Synthesis of Compound 8a ((S)-4-Benzyl-3-oxo-1,2,5-thiadiazolidine 1,1-dioxide)

Compound 7a (6.2 g; 25 mmol) in 50 mL dry THF was treated with 60% NaH (1.1 g; 27 mmol) at 0° C. and the reaction mixture was stirred at room temperature overnight. The solvent was removed in vacuo and the solid residue was triturated with ether, yielding the sodium salt of 7. This was dissolved in methanol (50 mL) and stirred with DOWEX 50X8-200 resin (20 g) for 2 h. The resin was filtered off and the solvent was removed, leaving behind crude 8a which was recrystallized from methanol (4.5 g; 80% yield), mp 196°–7° C. $^1$H NMR (CDCl$_3$): δ 8.28 (s,1H), 7.4–7.2 (m,6H), 3.45 (dd, 1H), 3.14 (dd, 1H), 2.88 (dd,1H); [α]$_D$–86.3 (c 1, CH$_3$OH). Anal. Calcd. for C$_9$H$_{10}$N$_2$O$_3$S: C,47.73; H, 4.61; N, 12.38. Found: C, 47.47; H, 4.61; N, 12.17.

iv) Synthesis of Compound 9a ((S)-4-Benzyl-2-hydroxymethyl-3-oxo-1.25-thiadazolidine 1.1-dioxide)

To a solution of compound 8a (0.45 g; 2 mmol) in 2 mL of methanol was added 37% formaldehyde (0.38 g; 4.7 mmol). The solution was refluxed for two minutes and the solvent was allowed to evaporate off at room temperature. A crystalline material formed which was collected and washed with ether, yielding pure 9a (0.15 g; 30% yield). $^1$H NMR (acetone-d$_6$): δ 7.46–7.22 (m,5H), 7.14 (d, 1H), 5.77 (d, 1H), 5.12 (d,2H), 4.55 (m, 1H), 3.30 (dd, 1H), 3.00 (dd, 1H). Anal. Calcd. for C$_{10}$H12N2O$_4$S: C, 46.86; H, 4.72; N. 10.93. Found: C, 47.00; H, 4.81; N, 10.83.

v) Synthesis of Compound 1a ((S)-4-Benzyl-2-fluoromethyl-3-oxo-1,2,5-thiadiazolidine 1.1-dioxide)

To a suspension of compound 9a (0.70 g; 2.73 mmol) in 20 mL of dry methylene chloride kept in an ice bath was added dropwise a solution of diethylaminosulfurtrifluoride (DAST)(0.484 g; 3.00 mmol) in 20 mL methylene chloride. The reaction mixture was allowed to warm to room temperature and stirred for 0.5 h. Methylene chloride (15 mL) and water (15 mL) were added and the layers separated. The organic layer was dried and evaporated to give a crude product which was purified by flash chromatography: 1a (0.55 g; 78% yield), mp 92°–93° C.; $^1$H NMR (CDCl$_3$): δ 7.45–7.18 (m,5H), 5.70 (d,1H), 5.53 (d, 1H), 4.93 (s,1H), 4.48 (m, 1H), 3.33 (dd, 1H), 3.18 (dd, 1H); [α]$_D$–130.8 (c 2; methanol). Anal. Calcd. for C$_{10}$H$_{11}$N$_2$O$_3$FS: C, 46.50; H, 4.29; N, 10.85. Found: C, 46.50; H, 4.29; N, 10.88.

III. General Procedure for Preparing Compounds 2a–5a (FIG. 2).

To a solution of compound 1a (0.2 g; 0.774 mmol) in 3 mL dry acetonitrile kept in an ice bath, was added 60% sodium hydride (0.027 g; 0.70 mmol), followed by the appropriate alkylating agent (7.74 mmol), preferably CH$_3$I, C$_6$H$_5$CH$_2$Br, BrCH$_2$COOt-Bu, BrCH$_2$COOBzl. The reaction mixture was stirred overnight and the solvent was removed in vacuo. The residue was dissolved in 20 mL methylene chloride, washed with water (2×20 mL) and dried over anhydrous sodium sulfate. The isolated products were purified by flash chromatography.

i) Compound 2a ((S)-4-Benzyl-2-fluoromethyl-5-methyl-3-oxo-1,2,5-thiadiazolidine 1.1-dioxide)

mp 88.5°–90° C. $^1$H NMR: δ 7.42–7.20 (m,5H), 5.76–5.50 (m,2H), 4.10 (dd,1H), 3.32 (dd,1H), 3.13 (dd, 1H), 2.71 (s,3H). [α]D–89.4 (C 1, methanolmethylene chloride 5:1). Anal. Calcd. for ClH$_{13}$N$_2$O$_3$FS: C, 48.52; H, 4.81; N, 10.29. Found: C, 48.62; H, 4.90; N, 10.24.

ii) Compound 3a ((S)-4.5-Dibenzyl-2-fluoromethyl-3-oxo-1,2,5-thiadiazolidine 1.1-dioxide):

oil; $^1$H NMR: δ 7.40–7.05 (m,10H), 5.69 (s,1H), 5.52 (s,1H), 4.35 (d, 1H), 4.13 (dd,1H), 4.07 (d, 1H), 3.11 (m,2H). [α]$_D$–92.2 (c 1, CHCl$_3$). Anal. Calcd. C, 58.60; H, 4.92; N, 8.05. Found: C, 58.42; H, 4.89; N, 7.96.

iii) Compound 4a (S)-4-Benzyl-5(tert-butoxycarbonylmethyl)-2-fluoromethyl-3-oxo-1,2,5-thiadiazolidine 1.1-dioxide)

mp 124°–124.5° C. $^1$H NMR: δ 7.45–7.25 (m,5H), 5.76 (q, 1H), 5.59 (q, 1H), 4.41 (dd, 1H), 3.93 (dd, 1H), 3.30 (dd, 1H), 3.07 (dd, 1H), 3.03 (d, 1H), 1.42 (s,9H). [α]$_D$–62.6 (c 1, CHCl$_3$). Anal. Calcd. C, 51.60; H, 5.68; N, 7.52. Found: C, 51.51; H, 5.71; N, 7.52.

iv) Compound 5a (S) -Benzyl-5(benzyloxycarbonylmethyl)-2-fluoromethyl-3-oxo-1,2,5-thiadiazolidine 1.1-dioxide)

mp 79°–79.5° C. $^1$H NMR: δ 7.45–7.20 (m,10H), 5.68 (q, 1H), 5.50 (q, 1H), 5.09 (d,2H), 4.36 (dd, 1H), 4.09 (d,1H), 3.31 (dd,1H), 3.16 (d,1H), 3.04 (dd,1H). [α]$_D$–55.5 (c 1, CHCl$_3$). Anal. Calcd. C, 56.15; H 4.71; N, 6.89. Found: C, 55.98; H, 4.73; N, 6.82.

Those skilled in the art will appreciate that the starting reagent in FIG. 2 may be another amino acid ester so that the number 4 ring position of a 3-oxo-1,2,5 thiadiazolidine-1,1 dioxide can be modified. Preferably, (L)-Val-OCH$_3$ or (L)-Leu-OCH$_3$ are each used independently as starting reagents in order to introduce a lower alkyl group at the number 4 position of the 3-oxo-1,2,5-thiadiazolidine 1.1-dioxide ring (see FIG. 2). More preferably, (L)-Phe-OCH$_3$ is used to introduce a benzyl group in the number 4 ring position of the 3-oxo-1,2,5-thiadiazolidine 1,1-dioxide ring.

An important observation in the experiments described herein is that a side group at the number 4 position modulates the inhibitory action of a compound of the invention. Preferably, a benzyl group is introduced at the number 4 position in order to enhance inhibition of Cath G and chymotrypsin, or a small hydrophobic residue is introduced at the number 4 position (e.g. a loweralkyl) in order to enhance inhibition of elastase, or a basic group is introduced at the number 4 position (e.g. a lower alkyl-guanidine or lower alkyl-amine) in order to enhance inhibition of trypsin. To a lesser extent, an above-mentioned side group introduced at the number 5 ring position can also modulate serine protease inhibitory activity of a compound of the invention.

IV. Synthesis of Dual Action Compounds Comprising an Anti-inflammatory Agent (Table 1A)

A first serine protease inhibitory moiety consisting of isothiazolidin-3-one-1,1 dioxide or a derivative thereof, or 3-oxo-1,2,5-thiadiazolidine 1,1-dioxide or a derivative thereof, can each be combined independently with a second moiety consisting of a non-steroidal anti-inflammatory drug. Reduction or prevention of serine protease activity by the first moiety will lead to desirable cleavage and release of the second moiety at the site of serine protease activity. Such dual action compounds may be especially useful anti-inflammation drugs. A general synthetic procedure for making saccharin derivatives comprising a non-steriodal anti-inflammatory agent has been disclosed (Groutas, W. C. et al. *Bioorg. & Med. Chem.* 1(4) 273–277 (1993); herein incorporated by reference). Isothiazolidin-3-one 1,1-dioxide derivatives comprising a non-steroidal anti-inflammatory agent (Table 1A) can be made by refluxing a N-chloromethyl-isothiazolidin-3-one (0.68 g; 2.5 mmol), preferably a 4-lower alkyl-, or 4-aryl lower alkyl substituted N-chloromethyl-isothiazolidin-3-one, most preferably 4-benzyl-N-chloromethyl-isothiazolidin-3-one, triethylamine (0.25 g; 2.5 mmol) and a non-steroidal anti-inflammatory agent (2.5 mmol of any one of ibuprofen, diclofenac, ketoprofen, aspirin, 5-ASA (i.e. 5-aminosalicylic acid), fenoprofen, naproxen or derivatives thereof)) in 5 ml of dry acetonitrile for 4 hours. The solvent is evaporated and the residue taken up in methylene chloride (30 ml). The organic layer is washed with water (2×30 ml), dried over anhydrous sodium sulfate and the solvent evaporated yielding a crude material which is purified by flash chromatography using hexane/methylene chloride/ethyl ether as the eluting solvent. Compound X of Table 1 is prepared by refluxing N-chloromethyl-isothiazolidin-3-one 1,1-dioxide with N-(2-mercaptopropionyl)-glycine (Sigma) for several hours. The resulting residue containing compound X is washed and purified as described above.

i) Preparation of N-chloromethyl-isothiazolidin-3-one 1,1 dioxide and 3-oxo-1,2,5-thiadiazolidine 1,1-dioxide Chloromethyl Derivatives An isothiazolidin-3-one 1,1-dioxide, preferably 4-benzyl-isothiazolidin-3-one 1,1-dioxide (intermediate 6 of FIG. 1) (0.53 g; 2.35 mmol) is refluxed with 37% formaldehyde (0.71 g; 7.05 mmol) in 20 ml of 1:3 ethanol water solution for 1 hour and allowed to cool to room temperature. The precipitate is collected by suction filtration, washed with several portions of ethyl ether (5×10 ml) and dried to yield 0.53 g of precipitate (4-benzyl-2-(hydroxymethyl)-isothiazolidin-3-one, see 9A of FIG. 2). The entire precipitate is suspended in a solution of thionyl chloride (2.38 g; 20 mmol) in 3 ml dry ethyl ether for 3 days. The excess reagent was removed in vacuo and the residue taken up in methylene chloride (30 ml). The organic layer is washed with 5% aqueous sodium bicarbonate solution, dried over anhydrous sodium sulfate, filtered and the solvent removed to yield 0.5 g pure (91%) N-chloromethyl-isothiazolidin-3-one. Those skilled in the art will appreciate that a chloromethyl group can be added to a 3-oxo-1,2,5-thiadiazolidine 1,1-dioxide derivative as exemplified herein, in which the derivative bears a hydrogen attached to a ring nitrogen (number 2 or 5 ring position), or a hydrogen is attached to both ring nitrogens (both number 2 and 5 ring positions). Preferably 4,5-benzyl-3-oxo-1,2,5-thiadiazolidine 1,1-dioxide is used to make 4,5-benzyl-3-oxo-2-(chloromethyl)-1,2,5-thiadiazolidine 1,1-dioxide. Such derivatives can also be reacted with an anti-inflammatory agent as described above.

V. Synthesis of Compounds Comprising an Amino Acid Group

Compounds of the invention comprising an N-protected amino acid are disclosed in Table 3. In order to prepare these compounds, N-chloromethyl-isothiazolidin-3-one 1,1-dioxide (0.68 g; 2.5 mmol), triethylamine (0.25 g; 2.5 mmol) and an N-protected amino acid (2.5 mmol), preferably any one of CBZ-L-Phe, CBZ-D-Phe, CBZ-L-Pro, CBZ-D-Pro, CBZ-L-Ala, or CBZ-Gly, N-t-Boc-L-Phe, N-t-BOC-D-Phe, N-t-BOC-L-Pro, or N-t-BOC-D-Ala, are refluxed in 5 ml of dry acetonitrile for 4 hours. The solvent is evaporated and the residue was taken up in methylene chloride (30 ml). The organic layer is washed with 5% aqueous sodium bicarbonate solution, 5% aqueous HCL, water and dried over anhydrous sodium sulfate. The solvent is removed in vacuo, yielding a crude product that is purified by flash chromatography using hexane/methylene chloride as the eluting solvent. Those skilled in the art will appreciate that compounds comprising an N-protected amino acid can also be made from a 3-oxo-1,2,5-thiadiazolidine 1,1-dioxide derivative comprising at least one chloromethyl group (disclosed above), preferably 4,5-benzyl-3-oxo-2-(chloromethyl)-1,2, 5-thiadiazolidine 1,1-dioxide, by using the procedure outlined above. Those skilled in the art will also appreciate that N-protected amino acids can be de-protected by using well known chemical reactions. For example, the t-BOC protecting group can be conveniently removed by treatment with a mild acid, preferably HF or $F_3CCOOH$.

VI. Synthesis of Compounds Comprising an Ester Linkage

Compounds of the invention comprising an ester linkage (Table 4) can be made from a carboxylic acid. In order to prepare these compounds, N-chloromethyl-isothiazolidin-3-one (2 mmol), triethylamine (3 mmol) and a carboxylic acid (3 mmol), preferably $HOOCCH_2=CHC_6H_5$, $HOOCCH_2CH_2Ph$ (2C), $HOOCCH_2CH_2Ph$ (3C), or $HOOCCH=CH—SPh$ (6C, cis and trans) is individually refluxed in 10 ml of acetonitrile for 12 hours. The solvent is evaporated and the residue taken up in ethyl ether (30 ml). The organic layer was washed with 5% aqueous sodium bicarbonate solution, 5% aqueous HCL, water and dried over anhydrous sodium sulfate. The solvent is removed in vacuo, yielding a crude product which is purified by flash chromatography using hexane/methylene chloride as eluting solvents. Those skilled in the art will appreciate that compounds comprising an ester linkage can be made from a 3-oxo-1,2,5-thiadiazolidine 1,1-dioxide derivative comprising at least one chloromethyl group (disclosed above). Preferably 4,5-benzyl-3-oxo-2—(chloromethyl)-1,2,5-thiadiazolidine 1,1-dioxide, is used in the procedure outlined above. It is possible to oxidize compounds comprising a —S— linkage to —$SO_2$— with a 95% solution of m-chloroperbenzoic acid to obtain 4C, 5C, and 8C.

VII. Synthesis of Compounds Comprising a Substitution Group

In general, it is possible to prepare a variety of substituted isothiazolidin-3-ones by reacting an isothiazolidin-3-one 1,1-dioxide, preferably 4-benzyl-isothiazolidin-3-one 1,1-dioxide (3 mmol), with an alkylating agent (3 mmol) in the presence of a suitable base (e.g. NaH, or TEA (triethylamine)) and solvent (e.g. DMF (dimethylformamide), THF (tetrahydrofuran) or $CH_3CN$). Several substituted 4-benzyl-isothiazolidin-3-one 1,1-dioxide are disclosed in Table 5.

i) Preparation of 4-benzyl-2-(fluoromethyl)isothiazolidin-3-one 1,1 dioxide (1D)

A solution of DAST (diethylaminosulfurtrifluoride 0.8 g; 5 mmol) in 5 ml of dry THF is added dropwise to a solution of 4-benzyl-2—(hydroxymethyl)-isothiazolidin-3-one (1.27 g; 5 mmol; disclosed above) in 20 ml of dry THF at 15° C. After addition, the reaction is allowed to warm to room temperature and stirring is continued overnight. The solvent is removed under reduced pressure and the residue is taken up in methylene chloride (30 ml). The organic layer is washed with water (2×25 ml), dried over anhydrous sodium sulfate and solvent removed to yield 1.26 g crude 1D. The crude material is purified by flash chromatography using hexane/methylene chloride as eluent to yield 1.02 g of pure 1D.

ii) Preparation of Compound 6D 4-benzyl-isothiazolidin-3-one 1,1-dioxide is refluxed with ClCH$_2$SPh in TEA using CH$_3$CN as solvent for 2 hours. Crude 6D is purified by flash chromatography using hexane/methylene chloride as eluent.

iii) Preparation of Compound 13D

Compound 6D in 5 ml of methylene chloride is treated with m-chloroperbenzoic acid (0.3 g; 1.2 mmol) at 0° C. and stirred overnight at room temperature. The precipitate is filtered off and the filtrate is washed with 5% aqueous sodium bicarbonate. The organic layer is separated and dried over anhydrous sodium sulfate, filtered and the solvent removed to yield 0.35 g of crude product. The crude material is purified by flash chromatography using hexane/methylene chloride as eluent to yield 0.25 g (57%) pure 13D.

iv) Preparation of Compound 14D

Compound 6D (0.35 g; 1.0 mmol) in 5 ml of methylene chloride is treated with m-chloroperbenzoic acid (0.63 g; 2.2 mmol) at 0° C. and stirred overnight at room temperature. The solvent is evaporated off and the residue was triturated with ethyl ether (30 ml). The solid is collected, washed with ethyl ether and air dried to yield 0.34 g (90%) pure 14D.

v) Preparation of 15D 4-benzyl-isothiazolidin-3-one 1,1-dioxide is refluxed with ClCH$_2$SCH$_3$ in TEA with THF as solvent for 4 hours. The resulting compound is purified by flash chromatography using hexane/methylene chloride as eluent. 0.44 g of this compound is suspended in 5 ml of methylene chloride and treated with m-chloroperbenzoic acid (0.98 g; 3.39 mmol) at 0° C. and stirred overnight at room temperature. The precipitate is filtered off and the filtrate washed with 5% aqueous sodium carbonate. The organic layer is dried over anhydrous sodium sulfate, filtered the the solvent removed to yield 0.31 g of pure 15D.

vi) Preparation of 4-benzyl-2-[(dimethylphosphono)methyl] isothiazolidin-3-one 1,1 dioxide (8D)

Compound 2D (0.54 g; 2 mmol) and trimethyl phosphite (0.5 g; 4 mmol) are heated at 160° C. for 5 hours under nitrogen. The excess reagent is removed in vacuo, leaving behind a crude product which is purified by flash chromatography using ethyl ether/ethyl acetate as eluents. The amount of 8D obtainable is 0.12 g (17% yield).

vii) Preparation of Compound 5D 4-benzyl-isothiazolidin-3-one 1,1-dioxide is refluxed with BrCH$_2$CO$_2$Et in NaH with DMF as solvent for 16 hours. Crude 5D is purified by flash chromatography using hexane/methylene chloride as eluent.

viii) Preparation of Compound 7D 4-benzyl-isothiazolidin-3-one 1,1-dioxide is refluxed with BrCH$_2$COPh in NaH with DMF as solvent for 2 hours. Crude 7D is purified by flash chromatography using hexane/methylene chloride as eluting solvent.

ix) Preparation of 4-benzyl-2—(triazolylmethyl) isothiazolidin-3-one 1,1-dioxide (9D)

Compound 2D (0.41 g; 1.5 mmol) and 1,2,4 triazole sodium salt (0.5 g; 3 mmol) are stirred together in 5 ml of dry DMF at room temperature overnight. The resulting solution is poured into 50 ml ice-cold water and extracted with ethyl ether (2×30 ml). The combined organic layer is dried over sodium sulfate and the solvent removed to yield 0.28 g of crude product. The crude material is purified by flash chromatography using methylene chloride/ethyl ether as eluting solvents to yield 45 mg (10%) of pure 9D.

x) Preparation of 4-benzyl-2—(imidazolylmethyl) isothiazolidin-3-one 1,1 dioxide (10D)

Compound 2D (0.54 g; 2 mmol), imidazole (0.27 g; 4 mmol), anhydrous potassium carbonate (0.55 g; 4 mmol) are refluxed together in 15 ml of THF for 12 hours. The resulting solution is concentrated and the residue was taken up in methylene chloride (50 ml). The organic layer is washed with water (3×50 ml), dried over anhydrous sodium sulfate and the solvent removed to yield 0.73 g of crude 10D. The crude material is purified by flash chromatography using ethyl ether/ethyl acetate as eluents to yield 0.55 g (90% yield) of pure 10D.

xi) Preparation of Compound 11D 4-benzyl-isothiazolidin-3-one 1,1-dioxide was refluxed with BrCH$_2$CH=CHPh in TEA with THF as solvent for 5 hours. Crude 11D was purified by flash chromatography using hexane/methylene chloride as eluting solvent.

xii) Preparation of Compound 12D

Same preparation as for 11D, except BrCH$_2$CH=CH$_2$ was used as an alkylating agent.

Those skilled in the art will appreciate that compounds comprising a substitution group can also be made from 3-oxo-1,2,5-thiadiazolidine 1,1-dioxide or derivatives thereof. Preferably 4,5-benzyl-3-oxo-1,2,5-thiadiazolidine 1,1-dioxide is used in the procedure outlined above.

III. Synthesis of 3-oxo-1,2,5-thiadizolidine 1,1-dioxide Derivatives

Derivatives of 3-oxo-1,2,5-thiadizolidine 1,1-dioxide are disclosed in Tables 2(1A–5A) and 6(1E–37E). The synthesis of Compounds 1A–5A has been disclosed above.

i) Preparation of Compound 8E 4-benzyl-3-oxo-2-(hydroxymethyl)-1,2,5-thiadiazolidine 1,1-dioxide (1.64 g; 6.4 mmol) and 3.0 g (25 mmol) thionyl chloride in 20 ml of dried ether are stirred together at room temperature for 5 days. The solvent is evaporated and excess thionyl chloride removed in vacuo. The residue is dissolved in 30 ml of methylene chloride, washed with 5% sodium bicarbonate in saturated NaCl, dried over sodium sulfate, concentrated in vacuo and purified by flash chromatography over silica gel to give 1.2 g of pure 8E (68% yield). 4-benzyl-3-oxo-2-(hydroxymethyl)-1,2,5-thiadiazolidine 1,1-dioxide can be prepared by reacting 4-benzyl-3-oxo-1,2,5-thiadiazolidine 1,1,-dioxide (0.45 g, 2 mmol) in 2 ml of methanol with 0.38 g 37% formaldehyde. The resulting solution is heated for 1–2 minutes, solvent evaporated at room temperature and crystalline solid dried to yield 0.15 g (30% yield) of 4-benzyl-3-oxo-2—(hydroxymethyl)-1,2,5-thiadiazolidine 1,1-dioxide.

ii) Preparation of Compound 7E

The sodium salt of 4-benzyl-3-oxo-1,2,5-thiadiazolidine 1,1-dioxide (0.99 g, 4.0 mmol) chloracetonitrile (0.33 g, 4.4 mmol) in 10 ml of DMF are stirred together at 70° C. for 8 hours. The reaction mixture is poured into 100 ml water, and the product extracted with ether (3×80 ml). The ether solutions are combined, washed with a saturated sodium chloride solution, dried over sodium sulfate, concentrated in vacuo, and purified by flash chromatography over silica gel to give 0.51 g of pure 7E (48% yield).

iii) Preparation of Compound 19E 4-benzyl-3-oxo-1,2,5-thiadiazolidine 1,1-dioxide (0.59 g, 2 mmol) and triethylamine (0.4 g, 4 mmol) in 10 ml CH$_3$CN was added 1.42 g (10 mmol) of methyliodide. After refluxing the reaction mixture for 2 hours, the solvent was evaporated in vacuo. The residue was dissolved in 30 ml of methylene chloride, washed with 5% HCL in saturated NaCl, dried over sodium sulfate, concentrated in vacuo and purified by flash chromatography over silica gel to give 4.4 g (72% yield) of pure 19E.

iv) Preparation of Compound 20E 4-benzyl-3-oxo-1,2,5-thiadiazolidine 1,1-dioxide (0.57 g, 2 mmol), potassium carbonate (2.65 g, 20 mmol) and methyliodide (1.42 g 10 mmol) in 30 ml acetone were stirred together at room temperature for 3 days. The resulting solid was filtered, concentrated and purified by flash chromatography over silica gel to give 0.21 g (33% yield) of 20E.

v) Preparation of Compounds 9E, 21E

To a solution of 4-benzyl-3-oxo-1,2,5-thiadiazolidine 1,1-dioxide (1.13 g, 5 mmol) is added chloromethyl phenyl sulfide (0.79 g, 5 mmol) and triethylamine (0.5 g, 5 mmol) in 20 ml of dry acetonitrile. The mixture is refluxed for 5 hours then concentrated in vacuo. The residue is dissolved in 50 ml of methylene chloride, than washed with water. The organic phase is dried and concentrated to give crude 9E. Purification by flash chromatography over silica gel gave 1.1 g (63% yield) of pure 9E. Compound 9E (1 g, 2.9 mmol), methyliodide (2.8 g, 20 mmol), and potassium chromate (2.8 g, 20 mmol) is stirred together in 20 ml of acetone at room temperature for 2 days. The resulting solid is filtered and concentrated in vacuo. The resulting residue is dissolved in 40 ml of methylene chloride, washed in water, dried over sodium sulfate, concentrated and purified by flash chromatography over silica gel to give 0.59 g (56% yield) of pure 21E.

vi) Preparation of Compounds 22E, 30E, 18E and 33E

Compound 30E can be obtained by N-alkylation of a mixture of mono- and di-sodium salts of 4-benzyl-3-oxo-1,2,5-thiadiazolidine 1,1-dioxide with chloromethyl phenyl sulfide in DMF (60° C. for 3 hours) using the procedure disclosed for Compound 22E is obtained by oxidation with m-chloroperbenzoic acid. Compound 23E (0.5 g, 2 mmol) is mixed with NaH (0.08 g) and 10 equivalents of methyliodide in $CH_3CN$ at 0° C. The mixture is stirred at room temperature for 3 days. Solvent is removed in a rotoevaporator at 50° C. The residue is suspended in methylene chloride, and washed with water to yield compounds 18E and 33E. The products were purified as described above.

vii) Preparation of Compound 10E: Compound 9E (0.42 g, 1.2 mmol) and m-chloroperbenzoic acid (0.832 g, 2.6 mmol) are stirred in 10 ml of methylene chloride at room temperature overnight. The solvent is removed in vacuo, and the resulting solid triturated with 30 ml of ether/n-pentane (5:1). The solid was collected and dried to give 0.33 g (72% yield) of pure 10E.

viii) Preparation of Compound 11E

Compound 21E (0.217 g, 0.6 mmol) and m-chloroperbenzoic acid (0.38 g, 1.3 mmol) are stirred in 10 ml of methylene chloride at room temperature for two days. 20 ml of methylene chloride is added to the mixture, then washed with 5% $NaHCO_3$ in saturated NaCL, dried over sodium sulfate, concentrated and purified by flash chromatography over silica gel to give 0.11 g (47% yield) of pure 11E.

ix) Preparation of Compounds 29E and 12E

Compound 9E (0.35 g) is refluxed with n-butyliodide (0.2 g) in NaH (0.04 g) in order to form 0.22 g 29E in 54% yield. Compound 29E is oxidized with m-chloroperbenzoic acid (0.5 g) to form Compound 12E. The compounds were purified as described above.

x) Preparation of Compounds 31E and 13E

Compound 9E (0.3 g) is treated with 0.2 g (1.15 mmol) of $PhCH_2Br$ and 0.04 g NaH to form 0.29 g of Compound 31E. Compound 31E is oxidized with m-chloroperbenzoic acid (0.5 g) to form Compound 13E. The compounds were purified as described above.

xi) Preparation of Compounds 32E and 15E

Compound 9E (0.35 g, 1 mmol) is reacted with NaH (0.04 g) and t-cinnamylbromide (0.22 g) in methylene chloride to yield Compound 32E (0.44 g) in 95% yield. Compound 32E (0.139 g, 0.3 mmol) was oxidized with m-chloroperbenzoic acid to give Compound 15E (0.173 g). The compounds were purified as described above.

xii) Preparation of Compounds 2E, 26E and 5E

Compound 23E (0.43 g, 1.37 mmol) is suspended in methylene chloride oxidized with a 95% solution of m-chloroperbenzoic acid at 0° C. After oxidation the solution is allowed to warm to room temperature and was stirred overnight to yield Compound 2E (0.37 g, 78% yield). Compound 23E was reacted with $BrCH_2COOt$-BOC (0.68 g) and NaH (0.27 g) to yield 0.68 g Compound 26E (92% yield). Compound 26E (0.23 g, 0.5 mmol) is oxidized with m-chloroperbenzoic acid (0.47 g, 1.5 mmol) in 3 ml methylene chloride at room temperature overnight. Methylene chloride (30 ml) is added to the mixture, the mixture washed with saturated $NaHCO_3$, dried over sodium sulfate, and concentrated to yield 0.15 g 5E (60.7% yield). The products were purified as described above.

xiii) Preparation of Compounds 24E, 3E, 18E, and 35E

Compound 2E (0.7 g, 2.2 mmol) was reacted with NaH (0.096 g) and methyliodide (0.2 g) in methylene chloride to yield Compound 24E. Compound 24E (0.12 g) was suspended in methylene chloride and stirred with m-chloroperbenzoic acid (0.4 g) at room temperature overnight. The mixture was diluted with methylene chloride and washed with 5% $NaHCO_3$ (20 ml total). The organic phase was separated and dried over sodium sulfate to yield compound 3E. Compound 35E was stirred in n-chloroperbenzoic acid+methylene chloride at room temperature. The mixture was diluted with 3 ml of methylene chloride and washed with 5% $NaHCO_3$+5% $Na_2SO_3$ (20 ml total). The organic layer was separated, dried and purified by flash chromatography to yield 18E.

xiv) preparation of Compounds 16E and 25E

Compound 2E (0.63 g) suspended in acetonitrile and mixed with NaH (0.096 g) and n-butyliodide at 0° C. The mixture is stirred at 0° C. for 30 minutes then allowed to warm to room temperature overnight (constant stirring). The solvent is removed in vacuo, the residue dissolved in methylene chloride, washed with water and dried over sodium sulfate. The residue is purified by flash chromatography over silica gel with methylene chloride/hexane (5:3) as eluting solvent to give 0.22 g pure 25E. Compound 25E (0.15 g) is oxidized with 0.5 g m-chloroperbenzoic acid in methylene chloride to yield Compound 16E.

xv) Preparation of Compounds 28E and 34E

Compound 27E (3.12 g, 15 mmol) is stirred in THF with $ClCH_2SCH_3$ (20 mmol) and TEA at room temperature. The mixture is refluxed for 3 hours, the THF evaporated and residue suspended in methylene chloride, washed with water and dried over sodium sulfate. The residue was concentrated and purified by flash chromatography over silica gel with methylene chloride (90% in hexane) or methylene chloride/ether (9:1) to give pure crystalline 28E. Compound 28E can be oxidized with m-chloroperbenzoic acid to yield Compound 34E.

xvi) Preparation of Compounds 36E, 37E, 38E and 39E

Compound 14E is reacted with an amino acid alkyl ester, preferably alanine methyl ester, in the presence of carbonyldiimidazole and trifluoroacetic acid (TFA) forming 36E. It will be apparent that any amino acid alkyl ester can be used to displace a t-BOC protecting group present on a compound of the invention, preferably the t-BOC protecting group present on compounds 5E, 14E or 26E. In order to prepare 37E, t-BOC-Phe (L) (0.258 g, 1.2 mmol) is added to 3 ml of methylene chloride and DCC 91.2 mmol, dicyclohexylcarbodiimide) with stirring for 30 minutes at 0° C., followed by addition of 23E (0.314 g, 1 mmol) and pyridine (0.1 g 1.2 mmol) in methylene chloride (2–3 ml). After stirring for an additional 18 hours, standard thin layer chromatography is employed to demonstrate that most of starting compound 23E has been converted to 37E. The mixture is stirred an additional 6 hours and after this time, the residue is washed with 20–30 mls of methylene chloride, dried and purified by flash chromatography as described above. It will be apparent that any N-protected amino acid may be added to a t-Boc protected compound of the invention, preferably 5E, 14E or 26E, in order to add one or more amino acids to the number 4 ring nitrogen. The addition of one or more side groups at this position is capable of enhancing the serine protease inhibitory activity or the solubility of a compound of the invention.

It will be apparent to those skilled in the art that compounds 38E and 39E can be obtained by using the synthetic procedures outlined above. Related methods for coupling multiple amino acid residues to N-carboxy-alpha-dehydroamino acid anhydride has been disclosed (Shin, C-G. et al. *Bull. Chem. Soc. Jpn* 66, 1844–1846 (1993)).

IX. Protease Inhibition by Compounds of the Invention in vitro

An in vitro assay can be used to screen compounds of the invention for the ability to reduce or inhibit serine proteinase activity. The human leukocyte elastase (HLE), cathepsin G (Cath G), and proteinase-3 assays have each been described (Groutas et al., *J. Med. Chem.* 32:1607–1611, 1989; Groutas et al., *Arch. Biochem. Biophys.* 294:144–146, 1992; Kao et al., *J. Clin. Invest.* 82:1963–1973, 1988, each incorporated by reference herein). The pseudo first-order inactivation rate constants ($k_{obs}$) were obtained from plots of $\ln(v_t/v_o)$ vs t, and expressed in terms of the apparent second-order inactivation rate constant, $k_{obs}/[I]$ $M^{-1}$ $s^{-1}$ (Tables 1–7). Tables 1–7 disclose the activity of preferred compounds of the invention as inhibitors of HLE and Cath G. Table 7 discloses the activity of Compounds 4A (C) and 3E (D) as inhibitors of Proteinase-3 activity. Compounds (A) and (B) have been disclosed previously (Groutas et al., *Bioorganic and Med. Chem.* 1(4):273–277, 1993; Groutas et al., *J. Med. Chem.* 36:3178, 1993).

Serine proteinase activity in a cell or tissue extract can be detrimental to the successful biochemical purification of proteins. Compounds of the invention that reduce or inhibit HLE, Cath G or proteinase-3 activity in vitro can be added to a cell or tissue extract in order to reduce or inhibit endogenous serine proteinase activity. A compound of the invention can be dissolved in water and used at a concentration of 100 micrograms/ml of cell or tissue extract in order to reduce or inhibit endogenous serine proteinase activity.

VIII. Inhibition of Inflammation in vivo: Compounds of the invention which reduce or inhibit serine proteinase activity in vitro, and/or reduce or prevent neutrophil diapedesis in vivo are likely to be important anti-inflammatory agents. The in vivo assay disclosed below can be used to test compounds of the invention for toxicity and the ability to reduce or prevent inflammation.

a) Neutrophil Elastase Activity and Cell Number after Administration of Compound A or Compound B to Rats:

TABLE 8

| Animal | Total WBC × $10^6$ | PMN × $10^6$ | Elastase Activity | |
|---|---|---|---|---|
| | | | ΔOD/min/ml | Rate/$10^6$PMN |
| DRUG A: Elastase Activity in Peripheral Blood Neutrophils | | | | |
| DMSO | 12.4 | 3.4 | 0.05 | 0.0147 |
| DMSO | 4.6 | 0.97 | 0.05 | 0.052 |
| +Drug A | 46.0 | 41.4 | 0.55 | 0.014 |
| +Drug A | 55.0 | 45.7 | 0.70 | 0.015 |
| DRUG B: Elastase Activity in Peripheral Blood Neutrophils | | | | |
| DMSO | 44.0 | 10.12 | 0.175 | 0.0173 |
| DMSO | 36.0 | 7.2 | 0.075 | 0.0104 |
| +Drug B | 22.0 | 8.14 | 0.125 | 0.0154 |
| +Drug B | 15.0 | 3.15 | 0.05 | 0.0159 |

Method

Inhibitor A or B were each injected twice daily into the tail vein of a rat (8 mg/kg) over a period of three days. Inflammation was not induced in these rats. Injected rats displayed no overt signs of toxicity. As shown in Table 8, administration of Compound A or Compound B in vehicle (DMSO) did not reduce elastase activity in circulating neutrophils compared to vehicle-only controls. Therefore, compound A and compound B do not enter neutrophils in vivo, and each compound fails to inactivate neutrophil intracellular proteinase. WBC=white blood cells; PMN=polymorphonuclear leukocytes; The elastase assay has been disclosed above.

TABLE 9

| | Peripheral Blood Cell Distribution (%) | |
|---|---|---|
| Animal | Lymphocytes | Neutrophils |
| DMSO | 72 | 28 |
| DMSO | 79 | 21 |
| +Drug A | 10 | 90 |
| +Drug A | 17 | 83 |
| DMSO | 77 | 23 |
| DMSO | 80 | 20 |
| +Drug B | 63 | 37 |
| +Drug B | 79 | 21 |

Method

Compound A or Compound B were each administered twice daily for three days at a dose of 8 mg/kg. Inflammation was not induced in these rats. As shown in Table 9, Compound A in vehicle (DMSO) caused an increase in the number of neutrophils into the peripheral circulation compared to vehicle alone. However, Compound B did not cause an increase in neutrophil number. These data show that in the absence of inflammation, the aspirin moiety of Compound A can increase neutrophil cell number. However, substitution of the aspirin moiety with a fluorine atom, as found in Compound B, prevents an increase in neutrophil cell number. After Compound A administration, most of the circulating cells are morphologically mature, suggesting that IP demargination is at least partly responsible for the increase in neutrophil number.

ii) Inhibition of Neutrophil diapedesis after experimentally induced peritonitis Each compound (A–D) was individually injected into the tail vein of a rat in a single dose (8 mg/kg). After injection, peritonitis was induced in the rat by an IP (intraperitoneal) injection of 1 ml of a 0.1% soluble starch solution. After 4 hours, the peritoneal cavity was lavaged with saline in order to determine the number and type of cells responding to peritonitis. Cell numbers were determined by a Coulter counter and cell type (e.g. lymphocytes, neutrophils, macrophages and monocytes) by standard Cytospin and Giemsa staining. Cell number and type was evaluated after IP injection of saline (negative control, no inflammation), starch (positive control, inflammation) or starch with IV injection of an inhibitor (experimental, inflammation). Inhibitors were dissolved in DMSO prior to administration. The results of two separate experiments are shown in Table 10 below:

TABLE 10

EXPERIMENT 1
Abdominal Lavage Call Distribution (%)

| Animal | Lymphocytes | Neutrophils | Macrophages Monocytes |
|---|---|---|---|
| Control | 52 | 17 | 31 |
| Saline | 46 | 15 | 38 |
| Starch | 20 | 57 | 23 |
| Starch + Drug A | 28 | 44 | 38 |
| Starch + Drug B | 31 | 39 | 30 |

Total Number of Cells Lavaged at 4 Hours ($\times 10^6$)

| Animal | Total Cells | Lymphocytes | Neutrophils | Macrophages Monocytes |
|---|---|---|---|---|
| Control | 18 | 9.4 | 3.1 | 5.6 |
| Saline | 20 | 9.2 | 3.0 | 7.6 |
| Starch | 34 | 6.8 | 19.4 | 7.8 |
| Starch + Drug A | 25 | 7.0 | 11.0 | 7.6 |
| Starch + Drug B | 26 | 8.1 | 10.1 | 7.8 |

EXPERIMENT 2
Abdominal Lavage Call Distribution (%)

| Animal | Lymphocytes | Neutrophils | Macrophages Monocytes |
|---|---|---|---|
| Control | 35 | 16 | 49 |
| Saline + Drug B | 12 | 22 | 66 |
| Starch | 8 | 69 | 23 |
| Starch + Drug B | 31 | 39 | 30 |
| Starch + Drug C | 12 | 76 | 12 |
| Starch + Drug D | 20 | 56 | 24 |

Total Number of Cells Lavaged at 4 Hours ($\times 10^6$)

| Animal | Total Cells | Lymphocytes | Neutrophils | Macrophages Monocytes |
|---|---|---|---|---|
| Control | 20 | 7.0 | 3.2 | 9.8 |
| Saline + Drug B | 22 | 2.6 | 4.8 | 14.5 |
| Starch | 46 | 3.7 | 31.7 | 10.6 |
| Starch + Drug B | 32 | 9.9 | 12.5 | 9.6 |
| Starch + Drug C | 54 | 6.5 | 41.0 | 6.5 |
| Starch + Drug D | 32 | 6.4 | 17.9 | 7.7 |

As shown in Table 10 above, Compounds A and B reduced peritonitis induced neutrophil diapedesis by more than 50%. The increase in cell number in the abdominal lavage could be accounted for almost exclusively by the increase in neutrophil number, since in all animals, the total number of lymphocytes, macrophages and monocytes recovered by abdominal lavage remained constant during each experiment. Compound C, an inhibitor of Cath G, did not inhibit neutrophil diapedesis associated with peritonitis. Compound D, an elastase inhibitor, substantially reduced neutrophil diapedesis suggesting that it is a useful, non-toxic anti-inflammatory agent.

The data show that the in vivo assay described herein is an effective method for screening compounds of the invention for anti-inflammation activity. The data also show that compounds of the invention can be administered as prophylactic agents in order to reduce or prevent future inflammation.

It is well known in the art that cancer cells produce serine proteases in order to degrade the surrounding extracellular matrix. The degradation of the surrounding extracellular matrix allows cancer cells to metastasize. It will be apparent that the compounds of the invention which reduce or inhibit serine protease activity, and/or block neutrophil diapedesis, will also serve as effective anti-metastatic agents that can be used to reduce or block cancer cell metastasis.

Compounds of the invention may be tested for the capacity to reduce or prevent cancer cell metastasis by administering said compounds to any of the well known metastatic tumor-bearing rodents, preferably a transgenic mouse bearing an activated c-myc oncogene (Leder et al., *Cell* 45:485–495, 1986). Compounds of the invention which reduce or prevent cancer cell metastasis in the mouse are useful anti-metastatic agents.

XI. Administration of Compounds of the Invention

Compounds of the invention can be formulated into pharmaceutical compositions by admixture with pharmaceutically acceptable non-toxic excipients and carriers. Compounds of the invention may be prepared for use in parenteral administration, particularly in the form of liquid solutions or suspensions; for oral administration, particularly in the form of tablets or capsules; or intranasally, particularly in the form of powders, nasal drops, or aerosols.

A compound of the invention may be conveniently administered in unit dosage form and may be prepared by any of the methods well known in the pharmaceutical art, or example, as described in *Remington's Pharmaceutical Sciences* (Mack Pub. Co., Easton, Pa., 1980). Formulations for parenteral administration may contain as common excipients sterile water or saline, polyalkylene glycols such as polyethylene glycol, oils of vegetable origin, hydrogenated naphthalenes and the like. In particular, biocompatible, biodegradable lactide polymer, lactide/glycolide copolymer, or polyoxyethylene-polyoxypropylene copolymers may be useful excipients to control the release of a compound of the invention. Other potentially useful parenteral delivery systems include ethylene-vinyl acetate copolymer particles, osmotic pumps, implantable infusion systems, and liposomes. Formulations for inhalation administration contain as excipients, for example, lactose, or may be aqueous solutions containing, for example, polyoxyethylene-9-lauryl ether, glycocholate and deoxycholate, or oily solutions for administration in the form of nasal drops, or as a gel to be applied intranasally. Formulations for parenteral administration may also include glycocholate for buccal administration, methoxysalicylate for rectal administration, or citric acid for vaginal administration.

The concentration of a compound described herein in a pharmaceutically acceptable mixture will vary depending upon a number of factors, including the dosage of the compound to be administered, the chemical characteristics (e.g., hydrophobicity) of the compounds employed, and the route of administration. In general terms, the compounds of this invention may be provided in an aqueous physiological buffer solution containing about 0.1 to 10% w/v compound for parenteral administration. Typical dose ranges are from about 1 µg/kg to about 1 g/kg of body weight per day; a preferred dose range is from about 0.01 mg/kg to 100 mg/kg of body weight per day; most preferably 8 mg/kg of body weight per day. The preferred dosage of drug to be administered is likely to depend on such variables as the type and extent of inflammation or cancer metastasis, the overall health status of the particular patient, the relative biological efficacy of the compound selected, the formulation of the compound excipients, and its route of administration.

XII. Materials: Human leukocyte elastase was purchased from Elastin Products Co., Owensville, Mo.

Human leukocyte cathepsin G was obtained from Athens Research and Technology, Athens, Ga. Methoxysuccinyl Ala-Ala-Pro-Val p-nitroanilide and methoxysuccinyl Ala-Ala-Pro-Phe p-nitroanilide were purchased from Sigma Chemicals Co., St. Louis, Mo. Baker-analyzed 60–200 mesh silica gel was used for flash chromatography.

TABLE 1A

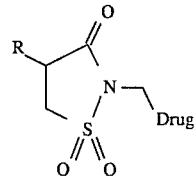

| Compound | R | Drug[b] | HLE[a] | Cath G[a] |
|---|---|---|---|---|
| 1' | benzyl | ibuprofen | 160 | 240 |
| 2' | " | diclofenac | 30 | 80 |
| 3' | " | ketoprofen | 210 | 290 |
| 4' | " | aspirin | 830 | 3000 |
| 5' | " | 5-ASA | 470 | 3330 |
| 6' | " | X | 90 | 2040 |

TABLE 1A-continued

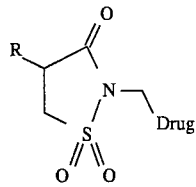

| Compound | R | Drug[b] | HLE[a] | Cath G[a] |
|---|---|---|---|---|

[a] $k_{obs}/[I]$ m$^{-1}$ s$^{-1}$;
[b] The linkage to the N-methylene carbon is with the carboxy group of each drug.

X is represented by the formula:

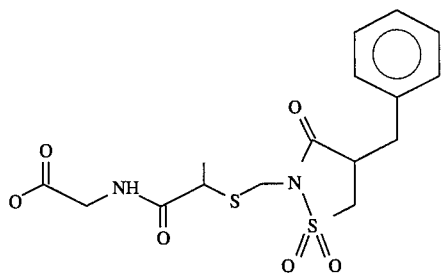

or X is —S—CH(CH$_3$)CONHCH$_2$COOH where the inhibiting activity with HLE and Cath G has not been assayed.

TABLE 1B

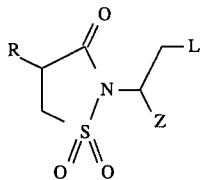

Inhibition of Human Leukocyte Elastase and Cathepsin G

| Compound | R | Z | L | Cath G | HLE |
|---|---|---|---|---|---|
| 7' | benzyl | SPh | F | 40 | a |
| 8' | benzyl | SO$_2$Ph | F | 420 | 50 |
| 9' | | | | 340 | b |

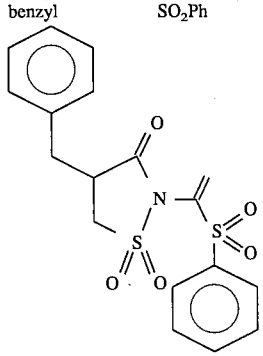

TABLE 1B-continued

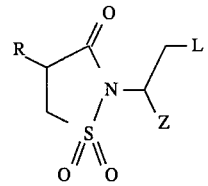

Inhibition of Human Leukocyte Elastase and Cathepsin G

| Compound | R | Z | L | Cath G | HLE |
|---|---|---|---|---|---|
| 10' | | | | 960 | c |

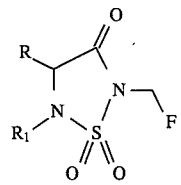

[a] 24% inhibition at an [I]/[E] ratio of 200 and a 10 minute incubation period.
[b] 20% inhibition at an [I]/[E] ratio of 200 and a 10 minute incubation period.
[c] 12% inhibition at an [I]/[E] ratio of 200 and a 10 minute incubation period.

TABLE 2

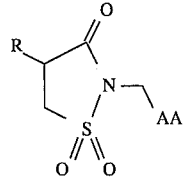

Inhibition of Human Leukocyte Elastase and Cathepsin G by Substituted 3-Oxo-1,2,5-Thiadiazolidine 1,1-Dioxides

| | | | $k_{obs}/[I]$ M$^{-1}$ s$^{-1}$ | |
|---|---|---|---|---|
| Compound | R | R$_1$ | HLE | Cath G |
| 1A | benzyl | H | NA | 600 |
| 2A | " | methyl | 1315 | 750 |
| 3A | " | benzyl | 930 | * |
| 4A | " | CH$_2$COOt-Bu | 490 | * |
| 5A | " | CH$_2$COOBzl | 810 | * |

*Inactivation was too rapid to measure by the sampling techniques described above.

TABLE 3

| Compound | R | AA | Cath G[a] | HLE[a] |
|---|---|---|---|---|
| 1B | benzyl | Cbz—L—Phe | 20 | 110 |

TABLE 3-continued

[Structure: R-CH-C(=O)-N(AA)-S(=O)₂-CH₂ cyclic sulfonamide]

| Compound | R | AA | Cath G[a] | HLE[a] |
|---|---|---|---|---|
| 2B | " | t-BOC—L—Phe | 10 | 680 |
| 3B | " | Cbz—D—Phe | 160 | 2300 |
| 4B | " | t-BOC—D—Phe | 260 | 1140 |
| 5B | " | Cbz—L—Pro | 7700 | 220 |
| 6B | " | t-BOC—L—Pro | 590 | 170 |
| 7B | " | Cbz—D—Pro | 360 | 520 |
| 8B | " | Cbz—L—Ala | 2770 | 50 |
| 9B | " | Cbz—D—Ala | 1820 | 300 |
| 10B | " | t-BOC—D—Ala | 560 | 310 |
| 11B | " | Cbz—Gly | 2680 | 220 |

[a] $k_{obs}/[I]\ M^{-1}\ s^{-1}$

TABLE 4

[Structure: R-CH-C(=O)-N(CH₂-O-C(=O)-R₁)-S(=O)₂ cyclic sulfonamide]

| | | | $k_{obs}/[I]\ M^{-1}\ s^{-1}$ | |
|---|---|---|---|---|
| Compound | R | R1 | Cath G | HLE |
| 1C | benzyl | t-styryl | 3220 | 280 |
| 2C | " | —CH₂CH₂Ph | 640 | 680 |
| 3C | " | —CH₂SPh | 3340 | 1020 |
| 4C–5C | " | —CH₂S(O)ₙPh | | |
| | | n = 1 | 770 | 320 |
| | | n = 2 | 1050 | 340 |
| 6C–7C | " | —CH=CH—SPh | | |
| | | cis | 7270 | 170 |

TABLE 4-continued

| | | | $k_{obs}/[I]\ M^{-1}\ s^{-1}$ | |
|---|---|---|---|---|
| Compound | R | R1 | Cath G | HLE |
| 8C | " | trans —CH=CH—SO₂Ph | 5520 2770 | 240 380 |

TABLE 5

[Structure: R-CH-C(=O)-N(CH₂-X)-S(=O)₂ cyclic sulfonamide]

| | | | $k_{obs}/[I]\ M^{-1}\ s^{-1}$ | |
|---|---|---|---|---|
| Compound | R | X | Cath G | HLE |
| 1D | benzyl | F | 2700 | 160 |
| 2D | " | Cl | 2040 | 670 |
| 3D–12D* | " | OH, —CN, —COOEt, —SPh, —CO—Ph, —PO(OCH₃)₂, triazole imidazole, trans-styryl, vinyl | | |
| 13D | " | —SO—Ph | 590 | NA |
| 14D | " | —SO₂—Ph | 960 | NA |
| 15D | " | —SO₂—CH₃ | 2080 | — |

*No Activity toward Cath G and HLE.

TABLE 6

[Structure: R₁-CH(NR₂)-C(=O)-N(CH₂-X)-S(=O)₂ cyclic sulfonamide]

| | | | | $k_{obs}/[I]\ M^{-1}\ s^{-1}$ | |
|---|---|---|---|---|---|
| Compd* | R₁ | R₂ | X | HLE | Cath G |
| 1E | benzyl | —SO₂Ph | SO₂Ph | NA | 830 |
| 2E | isobutyl | H | " | 190 | NA |
| 3E | " | methyl | " | 7580 | NA |
| 4E | " | —CH₂COOBzl | " | 1710 | NA |
| 5E | " | —CH₂COOt-BOC | " | 2020 | NA |
| 6E | benzyl | H | H | NA | 600 |
| 7E | " | H | CN | NA | NA |
| 8E | " | H | Cl | NA | 30 |
| 9E | " | H | SPh | NA | NA |
| 10E | " | H | SO₂Ph | NA | 30 |
| 11E | " | CH₃ | SO₂Ph | NA | 130 |
| 12E | " | n-butyl | " | NA | 320 |
| 13E | " | benzyl | " | NA | a |

TABLE 6-continued

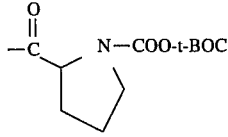

| Compd* | $R_1$ | $R_2$ | X | $k_{obs}/[I]$ $M^{-1}$ $s^{-1}$ HLE | Cath G |
|---|---|---|---|---|---|
| 14E | " | —CH$_2$COOt-BOC | " | NA | 1130 |
| 15E | " | t-cinnamyl | " | NA | 760 |
| 16E | isobutyl | n-butyl | " | 10640 | NA |
| 17E | " | benzyl | " | a | 440 |
| 18E | " | CH$_3$ | SO$_2$CH$_3$ | 4590 | NA |
| 19E | benzyl | H | CH$_3$ | NA | NA |
| 20E | " | CH$_3$ | " | NA | NA |
| 21E | benzyl | CH$_3$ | SPh | ND | ND |
| 22E | " | —CH$_2$SPh | SO$_2$Ph | ND | ND |
| 23E | isobutyl | H | SPh | NA | NA |
| 24E | " | CH$_3$ | " | NA | NA |
| 25E | " | N-butyl | " | ND | ND |
| 26E | " | —CH$_2$COOt-BOC | " | NA | NA |
| 27E | " | H | H | ND | ND |
| 28E | " | " | SCH$_3$ | ND | ND |
| 29E | benzyl | N-butyl | SPh | ND | ND |
| 30E | " | —CH$_2$SPh | " | NA | NA |
| 31E | " | benzyl | " | NA | NA |
| 32E | " | t-cinnamyl | " | ND | ND |
| 33E | isobutyl | CH$_3$ | I | ND | ND |
| 34E | " | H | SO$_2$CH$_3$ | ND | ND |
| 35E | " | CH$_3$ | SCH$_3$ | ND | ND |
| 36E | benzyl | —CH$_2$CONHCHCOOCH$_3$<br>          |<br>         CH$_3$ | SO$_2$Ph | ND | ND |
| 37E | isobutyl | (see structure) | SPh | ND | ND |
| 38E | benzyl | —COCH$_2$NHCOO-t-BOC | SPh | ND | ND |
| 39E | " | —COCHNH-t-BOC<br>        |<br>       CH$_3$ | SPh | ND | ND |

*all compounds have the S configuration
a inactivation was too fast to measure by sampling techniques at an [I]/[E] = 5;
NA = No Activity;
ND = Not Done

TABLE 7

| Compound | % Proteinase-3 Inhibition |
|---|---|
| 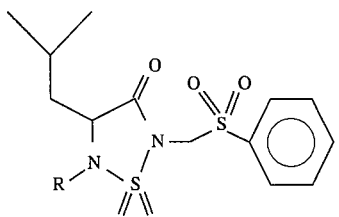<br>R = methyl<br>   benzyl | 84<br>86 |

TABLE 7-continued

| Compound | % Proteinase-3 Inhibition |
|---|---|
| 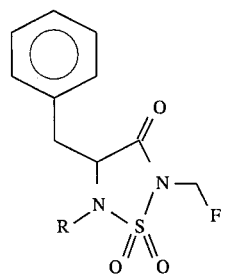 | |

TABLE 7-continued

| Compound | % Proteinase-3 Inhibition |
|---|---|
| R = methyl | 55 |
| benzyl | 43 |
| CH$_2$COOt-BOC | 33 |
| 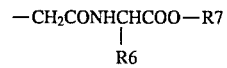 | 79 |
| 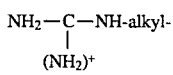 | 66 |
| 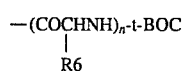 | inactive |

What is claimed is:

1. A compound represented by the following formula:

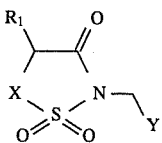

a) X is CH2 or NR2 where R2 is any one of H, alkyl, halogen substituted alkyl, alkenyl, halogen substituted alkenyl, alkynyl, halogen substituted alkynyl, halogen substituted alkanoate, alkoxy, Ph-alkyl-, Ph-alkenyl-, Ph-alkynyl-, Ph—S-alkynyl-, —Ph—S-alkyl-, Ph—S-alkenyl-, Ph—S-alkynyl-, Ph—SO—, Ph—SO$_2$—, Ph—SO$_2$-alkyl-, Ph—SO$_2$-alkenyl-, Ph—SO$_2$-alkynyl-, benzyl, alkyl substituted benzyl, alkenyl substituted benzyl, alkynyl substituted benzyl, hydroxy substituted benzyl, alkoxy substituted benzyl, halogen substituted benzyl, aryl, —(CH$_2$)$_n$COOR5 where n is 1 to 5 inclusive and R5 is any one of H, alkyl, alkenyl, alkynyl, halogen substituted alkanoate, N-tert-butoxy carbonyl (t-BOC), benzyl, alkyl substituted benzyl, alkenyl substituted benzyl, alkynyl substituted benzyl, hydroxy substituted benzyl, halogen substituted benzyl, —SO$_2$Ph, —SO$_2$-alkane, —SO$_2$-alkene, —SO$_2$-alkyne, —S—Ph, Ph—S-alkyl-, Ph—S-alkenyl-, Ph—S-alkynyl-,

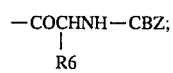

where R6 is any one of alkyl, benzyl, hydroxy substituted benzyl, indolyl-alkyl-, sulfhydryl-alkyl-, CH$_3$—S-alkyl-,

where R8 is H or methyl, imidazolyl-alkyl-, amide-alkyl- -amine-alkyl- or $$NH_2-C-NH\text{-alkyl-}$$
$$|$$
$$(NH_2)^+$$

and R7 is H or alkyl,

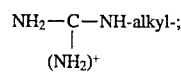

where n is 1 to 50 inclusive, or

b) R1 is any one of H, alkyl, benzyl, hydroxy substituted benzyl, indolyl-alkyl-, sulfhydryl-alkyl-, CH$_3$—S-alkyl-, $$HOCH—,$$
$$|$$
$$R8$$

imidazolyl-alkyl-, amide-alkyl-, amine-alkyl- or $$NH_2-C-NH\text{-alkyl-};$$
$$|$$
$$(NH_2)^+$$

and c) Y is

1) CBZ-(AA)$_n$ where b is 1 to 5 inclusive, and (AA) is selected from the group consisting of L-Phenylalanine, D-Phenylalanine, L-proline, D-proline, L-alanine, D-alanine, and glycine, N-t-BOC (AA)$_n$ where n is 1 to 5 inclusive, and (AA) is selected from the group consisting of L-phenylalanine, D-Phenylalanine, L-proline, D-proline, L-alanine, D-alanine, and glycine, Cl, F, Br, I, —SPh, Ph—SO—, —COO-alkane, —COO-alkene, —COO-alkyne, —PO(OCH$_3$)$_2$, —SO$_2$—Ph, —SO$_2$-alkane, —SO$_2$-alkene, —SO$_2$-alkyne, —S-alkane, —S-alkene, or —S-alkyne;

or

2) —O—CO—R3 where R3 is any one of H, alkyl, halogen substituted alkyl, alkenyl, halogen substituted alkenyl, alkynyl, halogen substituted alkynyl, Ph—S-alkyl-, Ph—S-alkenyl-, Ph—S-alkynyl-, Ph—SO$_2$-alkyl-, Ph—SO$_2$-alkenyl-, or Ph—SO$_2$-alkynyl-;

or 3) represented by the following formula:

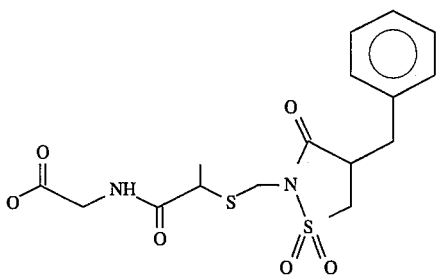

or

4)

where R4 is alkyl, halogen substituted alkyl, alkenyl, halogen substituted alkenyl, alkynyl, or halogen substituted alkynyl;

c) when R1 is benzyl and R2 is H, then Y cannot be F; or a pharmaceutically acceptable salt thereof.

2. A compound represented by the following formula:

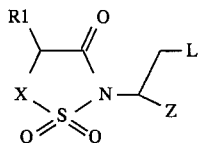

wherein:

a) X is CH2 or NR2 where R2 is any one of H, alkyl, halogen substituted alkyl, alkenyl, halogen substituted alkenyl, alkynyl, halogen substituted alkynyl, halogen substituted alkanoate, alkoxy, Ph-alkyl-, Ph-alkenyl-, Ph-alkynyl-, Ph—S-alkyl-, Ph—S-alkenyl-, Ph—S-alkynyl-, Ph—SO—, Ph—SO$_2$—, Ph—SO$_2$-alkyl-, Ph—SO$_2$-alkenyl-, PhSO$_2$-alkynyl-, benzyl, alkyl substituted benzyl, alkenyl substituted benzyl, alkynyl substituted benzyl, hydroxy substituted benzyl, alkoxy substituted benzyl, halogen substituted benzyl, aryl, —(CH$_2$)$_n$COOR5 where n is 1 to 5 inclusive and R5 is any one of H, alkyl, alkenyl, alkynyl, halogen substituted alkanoate, N-tert-butoxy carbonyl (t-BOC), benzyl, alkyl substituted benzyl, alkenyl substituted benzyl, alkynyl substituted benzyl, hydroxy substituted benzyl, halogen substituted benzyl, —SO$_2$—Ph, —SO$_2$-alkane, —SO$_2$-alkene, —SO$_2$-alkyne, —S—Ph, Ph—S-alkyl-, Ph—S-alkenyl-, Ph—S-alkynyl-,

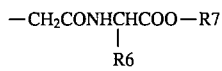

where R6 is any one of H, alkyl, benzyl, hydroxy substituted benzyl, indolyl-alkyl-, sulfhydryl-alkyl-, CH$_3$—S-alkyl,

where R8 is H or methyl, imidazolyl-alkyl-, amide-alkyl-, amine-alkyl- or

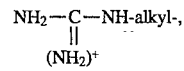

and R7 is H or alkyl,

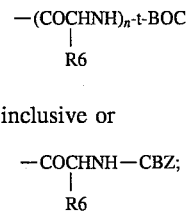

where n is 1 to 50 inclusive or

b) R1 is any one of H, alkyl, benzyl, hydroxy substituted benzyl, indolyl-alkyl-, sulfhydryl-alkyl-, CH$_3$—S-alkyl-,

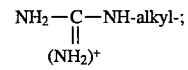

imidazolyl-alkyl-, amide-alkyl-, amine-alkyl- or $$NH_2-\underset{\underset{(NH_2)^+}{\|}}{C}-NH\text{-alkyl-};$$

c) L is H, F, Cl, Br or I;

d) Z is F, Cl, Br, I, CN, benzyl, alkyl substituted benzyl, alkenyl substituted benzyl, alkynyl substituted benzyl, halogen substituted benzyl, —SO$_2$PH, —SO$_2$-alkane, —SO$_2$-alkene, —SO$_2$-alkyne, —S—Ph, Ph—S-alkyl-, Ph—S-alkenyl-, Ph—S-alkynyl-, or aryl;

or a pharmaceutically acceptable salt thereof.

3. A method for treating inflammation in a mammal, said inflammation involving the unmodulated activity of a serine protease, said method comprising administering a compound of the general formula:

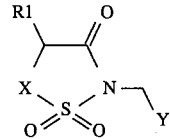

wherein:

a) X is CH2 or NR2 where R2 is any one of H, alkyl, halogen substituted alkyl, alkenyl, halogen substituted alkenyl, alkynyl, halogen substituted alkynyl, halogen substituted alkanoate, alkoxy, Ph-alkyl-, Ph-alkenyl-, Ph-alkynyl-, Ph—S-alkyl-, Ph—S-alkenyl-, Ph—S-alkynyl-, Ph—SO—, Ph—SO$_2$—, Ph—SO$_2$-alkyl-, Ph—SO$_2$-alkenyl-, Ph—SO$_2$-alkynyl-, benzyl, alkyl substituted benzyl, alkenyl substituted benzyl, alkynyl substituted benzyl, hydroxy substituted benzyl, alkoxy substituted benzyl, halogen substituted benzyl, aryl, —(CH$_2$)$_n$COOR5 where n is 1 to 5 inclusive and R5 is any one of H, alkyl, alkenyl, alkynyl, halogen substituted alkanoate, N-tert-butoxy carbonyl (t-BOC), benzyl, alkyl substituted benzyl, alkenyl substituted benzyl, alkynyl substituted benzyl, hydroxy substituted benzyl, halogen substituted benzyl, —SO$_2$Ph, —SO$_2$-alkane, —SO$_2$-alkene, —SO$_2$-alkyne, —S—Ph, Ph—S-alkyl-, Ph—S-alkenyl-, Ph—S-alkynyl-,

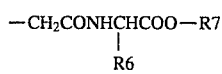

where R6 is any one of H, alkyl, benzyl, hydroxy substituted benzyl, indolyl-alkyl-, sulfhydryl-alkyl-, $CH_3$—S-alkyl-,

where R8 is H or methyl, imidazolyl-alkyl-, amide-alkyl-, -amine-alkyl- or

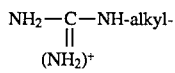

and R7 is H or alkyl;

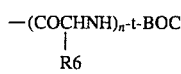

where n is 1 to 50 inclusive, or

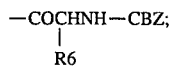

b) R1 is any one of H, alkyl, benzyl, hydroxy substituted benzyl, indolyl-alkyl-, sulfhydryl-alkyl-, $CH_3$—S-alkyl-,

imidazolyl-alkyl-, amide-alkyl-, amine-alkyl- or

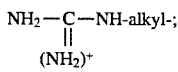

and c) Y is
1) CBZ-(AA)$_n$ where n is 1 to 5 inclusive, and (AA) is selected from the group consisting of L-Phenylalanine, D-phenylalanine, L-proline, D-proline, L-alanine, D-alanine, and glycine, N-t-BOC(AA)$_n$ where n is 1 to 5 inclusive, and (AA) is selected from the group consisting of L-phenylalanine, D-Phenylalanine, L-proline, D-proline, L-alanine, D-alanine, and glycine, Cl, F, Br, I, —SPh, Ph—SO—, —COO-alkane, —COO-alkene, -COO-alkyne, —PO(OCH$_3$)$_2$, —SO$_2$—Ph, —SO$_2$-alkane, —SO$_2$-alkene, —SO$_2$-alkyne, —S-alkane, —S-alkene, —S-alkyne;

or
2) —O—CO—R3 is any one of H, alkyl, halogen substituted alkyl, alkenyl, halogen substituted alkenyl, alkynyl, halogen substituted alkynyl, Ph—S-alkyl-, Ph—S-alkenyl-, Ph—S-alkynyl-, Ph—SO$_2$-alkyl-, Ph—SO$_2$-alkenyl-, or Ph—SO$_2$-alkynyl-;

or 3) represented by the following formula:

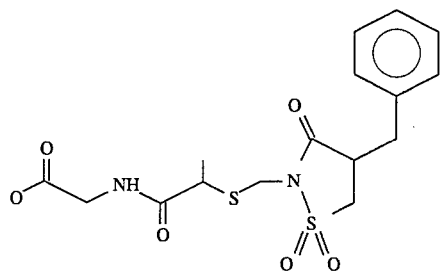

4)

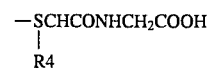

where R4 is alkyl, halogen substituted alkyl, alkenyl, halogen substituted alkenyl, alkynyl, or halogen substituted alkynyl;

c) and when R1 is benzyl and R2 is H, then Y cannot be F.

4. A method for treating inflammation in a mammal, said inflammation involving the unmodulated activity of a serine protease, said method comprising administering a compound of the general formula:

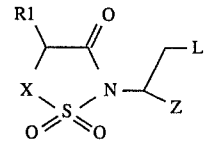

wherein:
a) X is $CH_2$ or NR2 where R2 is any one of H, alkyl, halogen substituted alkyl, alkenyl, halogen substituted alkenyl, alkynyl, halogen substituted alkynyl, halogen substituted alkanoate, alkoxy, Ph-alkyl-, Ph-alkenyl-, Ph-alkynyl-, Ph—S-alkyl-, Ph—S-alkenyl-, Ph—S-alkynyl-, Ph—SO—, Ph—SO$_2$—, Ph—SO$_2$-alkyl-, Ph—SO$_2$-alkenyl-, PhSO$_2$-alkynyl-, benzyl, alkyl substituted benzyl, alkenyl substituted benzyl, alkynyl substituted benzyl, hydroxy substituted benzyl, alkoxy substituted benzyl, halogen substituted benzyl, aryl, —(CH$_2$)$_n$COOR5 where n is 1 to 5 inclusive and R5 is any one of H, alkyl, alkenyl, alkynyl, halogen substituted alkanoate, N-tert-butoxy carbonyl (t-BOC), benzyl, alkyl substituted benzyl, alkenyl substituted benzyl, alkynyl substituted benzyl, hydroxy substituted benzyl, halogen substituted benzyl, —SO$_2$Ph, —SO$_2$-alkane, —SO$_2$-alkene, —SO$_2$-alkyne, —S—Ph, Ph—S-alkyl-, Ph—S-alkenyl-, Ph—S-alkynyl-,

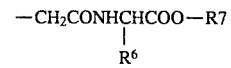

where R6 is any one of H, alkyl, benzyl, hydroxy substituted benzyl, indolyl-alkyl-, sulfhydryl-alkyl-, $CH_3$—S-alkyl-,

where R8 is H or methyl, imidazolyl-alkyl-, amide-alkyl-, amine-alkyl- or

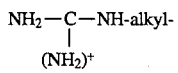

and R7 is H or alkyl,

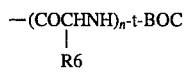

where n is 1 to 50 inclusive, or

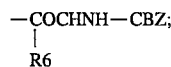

b) R1 is any one of H, alkyl, benzyl, hydroxy substituted benzyl, indolyl-alkyl-, sulfhydryl-alkyl-, $CH_3$—S-alkyl-,

imidazolyl-alkyl-, amide-alkyl-, amine-alkyl- or

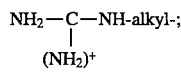

c) L is H, F, Cl, Br or I; and d) Z is F, Cl, Br, I, CN, benzyl, alkyl substituted benzyl, alkenyl substituted benzyl, alkynyl substituted benzyl, halogen substituted benzyl, —$SO_2$PH, —$SO_2$—alkane, —$SO_2$—alkene—, —$SO_2$-alkyne, —S—Ph, Ph—S-alkyl-, Ph—S-alkenyl-, Ph—S-alkynyl-, or aryl.

5. A method for reducing or inhibiting the activity of a serine protease, said method comprising:

contacting said serine protease with a compound of the general formula:

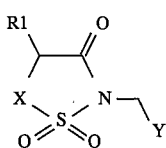

wherein:

a) X is CH2 or NR2 where R2 is any one of H, alkyl, halogen substituted alkyl, alkenyl, halogen substituted alkenyl, alkynyl, halogen substituted alkynyl, halogen substituted alkanoate, alkoxy, Ph-alkyl-, Ph-alkenyl-, Ph-alkynyl-, Ph—S-alkyl-, Ph—S-alkenyl-, Ph—S-alkynyl-, Ph—SO—, Ph—$SO_2$—, Ph—$SO_2$-alkyl-, Ph—$SO_2$-alkenyl-, Ph—$SO_2$-alkynyl-, benzyl, alkyl substituted benzyl, alkenyl substituted benzyl, alkynyl substituted benzyl, hydroxy substituted benzyl, alkoxy substituted benzyl, halogen substituted benzyl, aryl, —$(CH_2)_n$COOR5 where n is 1 to 5 inclusive and R5 is any one of H, alkyl, alkenyl, alkynyl, halogen substituted alkanoate, N-tert-butoxy carbonyl (t-BOC), benzyl, alkyl substituted benzyl, alkenyl substituted benzyl, alkynyl substituted benzyl, hydroxy substituted benzyl, halogen substituted benzyl, —$SO_2$Ph, —$SO_2$-alkane, —$SO_2$-alkene, —$SO_2$-alkyne, —S—Ph, Ph—S-alkyl-, Ph—S-alkenyl-, Ph—S-alkynyl-,

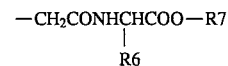

where R6 is any one of H, alkyl, benzyl, hydroxy substituted benzyl, indolyl-alkyl-, sulfhydryl-alkyl-, $CH_3$—S-alkyl-,

where R8 is H or methyl, imidazolyl-alkyl-, amide-alkyl-, -amine-alkyl- or

and R7 is H or

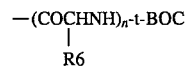

where n is 1 to 50 inclusive, or

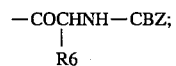

b) R1 is any one of H, alkyl, benzyl, hydroxy substituted benzyl, indolyl-alkyl-, sulfhydryl-alkyl-, $CH_3$—S-alkyl-,

imidazolyl-alkyl-, amide alkyl-, amine-alkyl- or

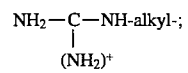

and c) Y is

1) CBZ-$(AA)_n$ where n is 1 to 5 inclusive, and (AA) is selected from the group consisting of L-phenylalanine, D-phenylalanine, L-proline, D-proline, L-alanine, D-alanine, and glycine, N-t-BOC$(AA)_n$ where n is 1 to 5 inclusive, and (AA) is selected from the group consisting of L-phenylalanine, D-phenylalanine, L-proline, D-proline, L-alanine, D-alanine, and glycine, Cl, F, Br, I, —Sph, Ph—SO—, —COO-alkane, —COO-alkene, -COO-alkyne, —$SO_2$—Ph, —$SO_2$-alkane, —$SO_2$-alkene, —$SO_2$-alkyne, —S-alkane, —S-alkene, —S-alkyne;

or

2) —O—CO—R3 where R3 is any one of H, alkyl, halogen substituted alkyl, alkenyl, halogen substituted alkenyl, alkynyl, halogen substituted alkynyl, Ph—S-alkyl-, Ph—S-alkenyl-. Ph—S-alkynyl-, Ph—$SO_2$-alkyl-, Ph—$SO_2$-alkenyl-, or Ph—$SO_2$-alkynyl-;

or 3) represented by the following formula:

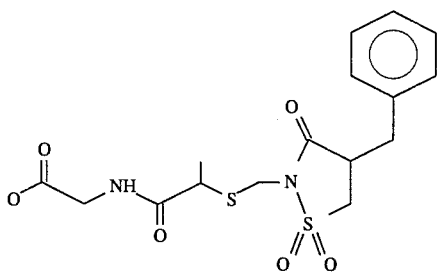

or

4)

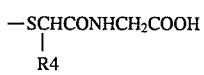

where R4 is alkyl, halogen substituted alkyl, alkenyl, halogen substituted alkenyl, alkynyl, or halogen substituted alkynyl;

c) when R1 is benzyl and R2 is H, then Y cannot be F.

6. A method for reducing or inhibiting the activity of a serine protease, said method comprising:

contacting said serine protease with a compound of the general formula:

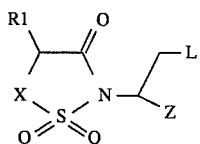

wherein:

a) X is CH2 or NR2 where R2 is any one of H, alkyl, halogen substituted alkyl, alkenyl, halogen substituted alkenyl, alkynyl, halogen substituted alkynyl, halogen substituted alkanoate, alkoxy, Ph-alkyl-, Ph-alkenyl-, Ph-alkynyl-, Ph—S-alkyl-, Ph—S-alkenyl-, Ph—S-alkynyl-, Ph—SO—, Ph—SO$_2$—, Ph—SO$_2$-alkyl-, Ph—SO$_2$-alkenyl-, PhSO$_2$-alkynyl-, benzyl, alkyl substituted benzyl, alkenyl substituted benzyl, alkynyl substituted benzyl, hydroxy substituted benzyl, alkoxy substituted benzyl, halogen substituted benzyl, aryl, —(CH$_2$)$_n$COOR5 where n is 1 to 5 inclusive and R5 is any one of H, alkyl, alkenyl, alkynyl, halogen substituted alkanoate, N-tert-butoxy carbonyl (t-BOC), benzyl, alkyl substituted benzyl, alkenyl substituted benzyl, alkynyl substituted benzyl, hydroxy substituted benzyl, halogen substituted benzyl, —SO$_2$Ph, —SO$_2$-alkane, —SO$_2$—alkene, —SO$_2$-alkyne, —S—Ph, Ph—S-alkyl-, Ph—S-alkenyl-, Ph—S-alkynyl-,

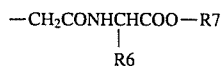

where R6 is any one of H, alkyl, benzyl, hydroxy substituted benzyl, indolyl-alkyl-, sulfhydryl-alkyl-, CH$_3$—S-alkyl-,

where R8 is H or methyl, imidazolyl-alkyl-, amide-alkyl-, amine-alkyl- or

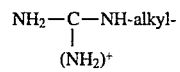

and R7 is H or alkyl,

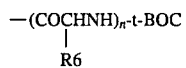

where n is 1 to 50 inclusive, or

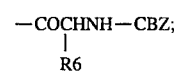

b) R1 is any one of H, alkyl, benzyl, hydroxy substituted benzyl, indolyl-alkyl-, sulfhydryl-alkyl-, CH$_3$—S-alkyl-,

imidazolyl-alkyl-, amide-alkyl- amine-alkyl- or

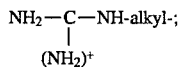

c) L is H, F, Cl, Br or I; and d) Z is F, Cl, Br, I, CN, benzyl, alkyl substituted benzyl, alkenyl substituted benzyl, alkynyl substituted benzyl, halogen substituted benzyl, —SO$_2$PH, —SO$_2$-alkane, —SO$_2$-alkene, —SO$_2$-alkyne, —S—Ph, Ph—S-alkyl-, Ph—S-alkenyl-, Ph—S-alkynyl-, or aryl.

7. The method of claim 3, wherein said inflammation is caused by tissue trauma, peritonitis, colitis, enteritis, vasculitis, pulmonary emphysema, chronic pulmonary infection, cystic fibrosis, bronchitis, arthritis, rheumatoid arthritis, psoriasis, allergic contact dermatitis, atopic dermatitis, glomerulonephritis, ARDS, pancreatitis or sepsis.

8. The method of claim 5, said serine protease being produced by cancer cells capable of metastasis.

9. The method of claim 5, said serine protease being elastase, Cath G, chymotrypsin, trypsin, or proteinase-3.

10. The method of claim 9, said elastase being human leukocyte elastase.

11. The method of claim 3, said mammal being a human.

12. The method of claim 5, said serine protease being present in a cell or tissue extract.

13. The method of claim 4, wherein said inflammation is caused by tissue trauma, peritonitis, colitis, enteritis, vasculitis, pulmonary emphysema, chronic pulmonary infection, cystic fibrosis, bronchitis, arthritis, rheumatoid arthritis, psoriasis, allergic contact dermatitis, atopic dermatitis, glomerulonephritis, ARDS, pancreatitis or sepsis.

14. The method of claim 6, said serine protease being produced by cancer cells capable of metastasis.

15. The method of claim 6, said serine protease being elastase, Cath G, chymotrypsin, trypsin, or proteinase-3.

16. The method of claim 15, said elastase being human leukocyte elastase.

17. The method of claim 4, said mammal being a human.

18. The method of claim 4, said mammal being a human.

19. The compound of claim 1, wherein X is NR2, where R2 is benzyl; R1 is alkyl; and Y is —SO$_2$Ph.

* * * * *